United States Patent
Fischer et al.

(10) Patent No.: US 6,861,391 B1
(45) Date of Patent: Mar. 1, 2005

(54) TRIFLUOROMETHYL-SUBSTITUTED SPIROCYCLIC KETOENOLS

(75) Inventors: Reiner Fischer, Monheim (DE); Alan Graff, Leverkusen (DE); Thomas Bretschneider, Lohmar (DE); Christoph Erdelen, Leverkusen (DE); Mark Wilhelm Drewes, Langenfeld (DE); Dieter Feucht, Monheim (DE)

(73) Assignee: Bayer Aktiengesellschaft, Leverkusen (DE)

( * ) Notice: Subject to any disclaimer, the term of this patent is extended or adjusted under 35 U.S.C. 154(b) by 130 days.

(21) Appl. No.: 10/088,979
(22) PCT Filed: Sep. 19, 2000
(86) PCT No.: PCT/EP00/09270
§ 371 (c)(1), (2), (4) Date: Mar. 26, 2002
(87) PCT Pub. No.: WO01/23354
PCT Pub. Date: Apr. 5, 2001

(30) Foreign Application Priority Data

Sep. 29, 1999 (DE) .......................... 199 46 625

(51) Int. Cl.$^7$ .................... C07D 209/96; C07D 307/94; C07C 255/46; A01N 43/12; A01N 43/38
(52) U.S. Cl. ...................... 504/283; 504/299; 514/409; 514/462; 548/408; 549/265; 558/426; 558/431; 560/43; 560/44; 560/61; 562/455
(58) Field of Search .................. 548/408; 549/265; 504/283, 299; 558/426, 431; 560/43, 44, 61; 562/455; 514/409, 462

(56) References Cited

U.S. PATENT DOCUMENTS

| | | | |
|---|---|---|---|
| 4,925,868 A | 5/1990 | Terao et al. ............... | 514/425 |
| 4,985,063 A | 1/1991 | Fischer et al. ............. | 71/88 |
| 5,045,560 A | 9/1991 | Fischer et al. ............. | 514/425 |
| 5,091,537 A | 2/1992 | Fischer et al. ............. | 546/226 |
| 5,094,681 A | 3/1992 | Krämer et al. ............. | 71/88 |
| 5,116,836 A | 5/1992 | Fischer et al. ............. | 514/224.2 |
| 5,186,737 A | 2/1993 | Fischer et al. ............. | 504/283 |
| 5,207,817 A | 5/1993 | Krämer et al. ............. | 504/299 |
| 5,258,527 A | 11/1993 | Krauskopf et al. .......... | 548/543 |
| 5,262,383 A * | 11/1993 | Fischer et al. ............. | 504/195 |
| 5,462,913 A | 10/1995 | Fischer et al. ............. | 504/138 |
| 5,504,057 A | 4/1996 | Fischer et al. ............. | 504/283 |
| 5,567,671 A | 10/1996 | Fischer et al. ............. | 504/283 |

(List continued on next page.)

FOREIGN PATENT DOCUMENTS

| | | | |
|---|---|---|---|
| EP | 528156 | * | 2/1993 |
| EP | 647637 | * | 4/1995 |
| EP | 668276 | * | 8/1995 |
| EP | 442077 | | 11/1995 |
| GB | 2266888 | | 11/1993 |
| WO | 94/29268 | | 12/1994 |
| WO | WO-95/26954 | * | 10/1995 |
| WO | WO-97/36868 | * | 10/1997 |
| WO | WO-98/05638 | * | 2/1998 |
| WO | 99/16748 | | 4/1999 |
| WO | 99/24437 | | 5/1999 |

OTHER PUBLICATIONS

Organikum, VEB Deutscher Verlag der Wissenschaften, Berlin (month unavailable), 1977, p. 505, "Darstellung von Benzoesäureestern durch Alkoholyse von Benzoylchlorid (Schotten–Baumann–Variante, allgemeine Arbeitsvorschrift für die qualitative Analyse)".

Chem. Reviews, (month Unavailable), 1952, pp. 237–416, Norman O. V. Sonntag, "The Reactions of Aliphatic Acid Chlorides".

Chem. Inc., 37, (month available), 1985, pp. 730–732, H. R. Ungerer, "Schiffsfarben–eine Spezialität der seenahen Lackindustrie".

(List continued on next page.)

Primary Examiner—Fiona T. Powers
(74) Attorney, Agent, or Firm—Richard E.L. Henderson

(57) ABSTRACT

Trifluoromethyl-substituted spirocyclic ketoenols of the formula (I) are provided

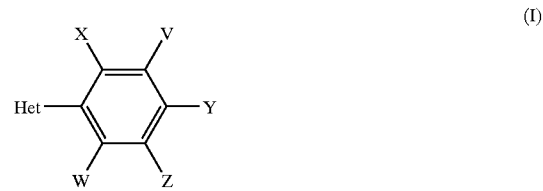

(I)

wherein
Het represents one of the groups

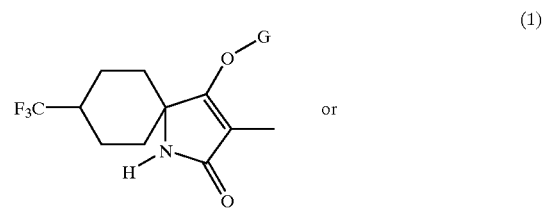

(1)

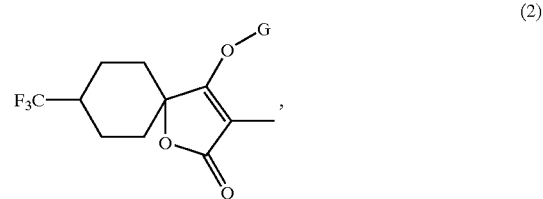

(2)

and G, V, W, X, Y, and Z are as defined in the specification. Also provides are processes for the preparation of the compounds. The compounds of formula (I) find use as pesticides.

21 Claims, No Drawings

U.S. PATENT DOCUMENTS

| | | | |
|---|---|---|---|
| 5,589,469 A | 12/1996 | Fischer et al. | 514/91 |
| 5,602,078 A | 2/1997 | Fischer et al. | 504/283 |
| 5,616,536 A | 4/1997 | Fischer et al. | 504/225 |
| 5,677,449 A | 10/1997 | Fischer et al. | 544/165 |
| 5,683,965 A | 11/1997 | Bachmann et al. | 504/238 |
| 5,994,274 A | 11/1999 | Fischer et al. | 504/282 |
| 6,110,872 A | 8/2000 | Lieb et al. | 504/284 |
| 6,200,932 B1 | 3/2001 | Fischer et al. | 504/225 |
| 6,251,830 B1 | 6/2001 | Fischer et al. | 504/251 |
| 6,288,102 B1 | 9/2001 | Hagemann et al. | 514/409 |
| 6,358,887 B1 | 3/2002 | Fischer et al. | 504/284 |
| 6,391,912 B1 | 5/2002 | Hagemann et al. | 514/444 |
| 6,469,196 B2 | 10/2002 | Fischer et al. | 560/105 |
| 6,511,942 B1 | 1/2003 | Lieb et al. | 504/299 |
| 2002/0022575 A1 | 2/2002 | Fischer et al. | 504/221 |
| 2002/0072617 A1 | 6/2002 | Hagemann et al. | 548/541 |
| 2002/0161034 A1 | 10/2002 | Hagemann et al. | 514/432 |

OTHER PUBLICATIONS

Liebigs Ann. Chem, (month unavailable) 1985, pp. 1095–1098, R. Schmierer et al, "Cyclisierung von N–Acylalanin–ung N–Acylglycinestern".

Chem. Pharm. Bull, 15 (8), (month unavailable) 1967, pp. 1120–1122, S. Suzuki et al, "Studies on Antiviral Agents. Biological Activity of Tenuazonic Acid Derivatives."

Ann. Chim., (month unavailable) 1970, t. 5, pp. 11–22, P. L. Compagnon et M. Miocque, "Addition Des Réactifs Nucleophiles Sur La Triple Liaison Nitrile. I. Addition Des Hydrures, De L'Eau, De L'Hydrogène SulfurèEt De L'Hydrogène Sélénié".

Ann. Chim., (month unavailable) 1970, t. 5, pp. 23–38, P. L. Compagnon et M. Miocque, "Addition Des Réactifs Nucleophiles Sur La Triple Liaison Nitrile. II. Addition Des Alcools, Des Composés Azotés, Des Organométalliques; Condensation de Plusieurs Molécules de Nitriles (*)".

Can. J. Chem., 53 (month unavailable), 1975, pp. 3339–3349, J. T. Edward et al, "Stereochemistry of the Bucherer–Bergs and Strecker Reactions of 4–tert–Butylcyclohexanone".

J. Chem. Soc., (month unavailable) 1961, pp. 4377–4379, L. Munday, "Amino–acids of the Cyclohexane Series. Part 1."

Indian J. Chem., 6, (month unavailable), 1968, pp. 341–345, B. Bhattacharya, "Isoquinoline Derivatives: Part XVII–Formation of 1–Alkyl–(or alkaryl or aryl)–3–methyl–7–chloro–(or 5–chloro)–isoquinolines".

* cited by examiner

TRIFLUOROMETHYL-SUBSTITUTED SPIROCYCLIC KETOENOLS

FIELD OF THE INVENTION

The present invention relates to novel trifluoromethyl-substituted spirocyclic ketoenols, to a plurality of processes for their preparation and to their use as pesticides and herbicides.

BACKGROUND OF THE INVENTION

Pharmaceutical properties of 3-acyl-pyrrolidine-2,4-diones have been described (S. Suzuki et al. Chem. Pharm. Bull. 15 1120 (1967)). Furthermore, N-phenylpyrrolidine-2,4-diones have been synthesized by R. Schmierer and H. Mildenberger (Liebigs Ann. Chem. 1985 1095). A biological activity of these compounds has not been described.

EP-A-262 399 and GB-A-2 266 888 disclose compounds of a similar structure (3-aryl-pyrrolidine-2,4-diones); however, a herbicidal, insecticidal or acaricidal activity of these compounds is not known. Known to have herbicidal, insecticidal or acaricidal activity are unsubstituted bicyclic 3-aryl-pyrrolidine-2,4-dione derivatives (EP-A-355 599 and EP-A-415 211) and substituted monocyclic 3-aryl-pyrrolidine-2,4-dione derivatives (EP-A-377 893 and EP-A-442 077).

Also known are polycyclic 3-arylpyrrolidine-2,4-dione derivatives (EP-A-442 073) and 1H-arylpyrrolidine-dione derivatives (EP-A-456063, EP-A-521 334, EP-A-596 298, EP-A-613 884, EP-A-613 885, WO 94/01 997, WO 95/26 954, WO 95/20 572, EP-A-0 668 267, WO 96/25 395, WO 96/35 664, WO 97/01 535, WO 97/02 243, WO 97/36 868, WO 98/05 638, WO 98/06 721, WO 98/25 928, WO 99/16 748 and WO 99/24 437).

It is known that certain substituted $\Delta^3$-dihydrofuran-2-one derivatives have herbicidal properties (cf. DE-A-4 014 420). The synthesis of the tetronic acid derivatives used as starting materials (such as, for example, 3-(2-methyl-phenyl)-4-hydroxy-5-(4-fluorophenyl)-$\Delta^3$-dihydrofuran-2-one) has also been described in DE-A-4 014 420. Compounds of a similar structure are known from the publication Campbell et al., J. Chem. Soc., Perkin Trans. 1, 1985 (8) 1567–76, but an insecticidal and/or acaricidal activity has not been mentioned. Also known, from EP-A-528 156, EP-A-647 637, WO 95/26 345, WO 96/20 196, WO 96/25 395, WO 96/35 664, WO 97/01 535, WO 97/02 243, WO 97/36 868, WO 98/05 638, WO 99/16 748 and WO 98/25 928, are 3-aryl-$\Delta^3$-dihydrofuranone derivatives having herbicidal, acaricidal and insecticidal properties. 3-Aryl-$\Delta^3$-dihydrothiophenone derivatives are also known (WO 95/26 345, WO 96/25 395, WO 97/01 535, WO 97/02 243, WO 97/36 868, WO 98/05 638, WO 98/25 928, WO 99/16 748).

However, the herbicidal, acaricidal and insecticidal activity and/or the activity spectrum and the compatibility of these compounds with plants, in particular with respect to crop plants, is not always sufficient.

DETAILED DESCRIPTION OF THE INVENTION

This invention now provides novel compounds of the formula (I)

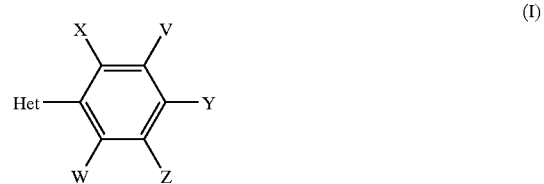

(I)

in which

V represents hydrogen, halogen, alkyl or alkoxy,

W represents hydrogen, cyano, nitro, halogen, alkyl, alkenyl, alkinyl, alkoxy, halogenoalkyl, halogenoalkoxy, in each case optionally substituted phenyl, phenoxy, phenylthio, phenylalkoxy or phenylalkylthio, X represents halogen, alkyl, alkenyl, alkinyl, alkoxy, halogenoalkyl, halogenoalkoxy, cyano, nitro, in each case optionally substituted phenyl, phenoxy, phenylthio, phenylalkyloxy or phenylalkylthio, Y represents hydrogen, halogen, alkyl, alkoxy, halogenoalkyl, halogenoalkoxy, cyano or nitro, Z represents hydrogen, halogen, alkyl, alkoxy, halogenoalkyl, halogenoalkoxy, hydroxyl, cyano, nitro or in each case optionally substituted phenoxy, phenylthio, 5- or 6-membered hetaryloxy, 5- or 6-membered hetarylthio, phenylalkyloxy or phenylalkylthio, Het represents one of the groups

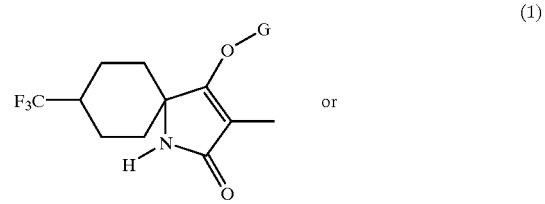

(1)

or

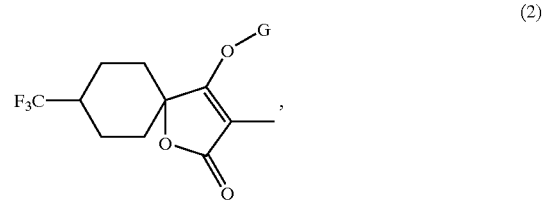

(2)

in which

G represents hydrogen (a) or represents one of the groups

(b)

(c)

(d)

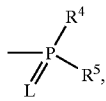
(e)

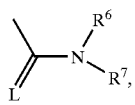
E, or (f)
(g)

in which

E represents a metal ion or an ammonium ion,

L represents oxygen or sulphur,

M represents oxygen or sulphur, $R^1$ represents in each case optionally halogen- or cyano-substituted alkyl, alkenyl, alkoxyalkyl, alkylthioalkyl or polyalkoxyalkyl or represents in each case optionally halogen-, alkyl- or alkoxy-substituted cycloalkyl or heterocyclyl or represents in each case optionally substituted phenyl, phenylalkyl, hetaryl, phenoxyalkyl or hetaryloxyalkyl, $R^2$ represents in each case optionally halogen- or cyano-substituted alkyl, alkenyl, alkoxyalkyl or polyalkoxyalkyl or represents in each case optionally substituted cycloalkyl, phenyl or benzyl, $R^3$, $R^4$ and $R^5$ independently of one another represent in each case optionally halogen-substituted alkyl, alkoxy, alkylamino, dialkylamino, alkylthio, alkenylthio or cycloalkylthio or represent in each case optionally substituted phenyl, benzyl, phenoxy or phenylthio, $R^6$ and $R^7$ independently of one another represent hydrogen, represent in each case optionally halogen- or cyano-substituted alkyl, cycloalkyl, alkenyl, alkoxy, alkoxyalkyl, represent in each case optionally substituted phenyl or benzyl, or together with the N atom to which they are attached form an optionally substituted cycle which optionally contains oxygen or sulphur, except for the compound I-a-79 from EP 528 156

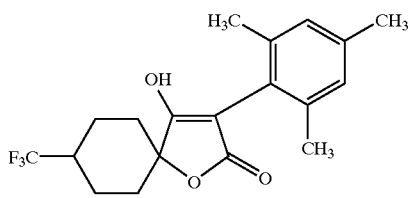

Depending, inter alia, on the nature of the substituents, the compounds of the formula (I) can be present as optical isomers or mixtures of isomers in varying compositions, which can be separated, if desired, in a customary manner. The present invention provides both the pure isomers and the isomer mixtures, their preparation and use and also compositions comprising them. In the following text, for simplicity, however, the compounds of the formula (I) are always referred to, although both pure compounds and, if appropriate, mixtures having different proportions of isomeric compounds are intended.

Including the meanings (1) to (2) of the group Het, the following principal structures (I-1) to (I-2) result:

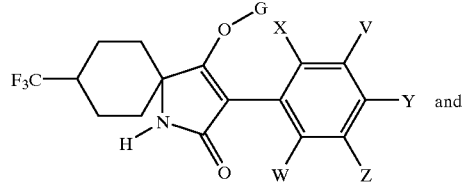
(I-1)

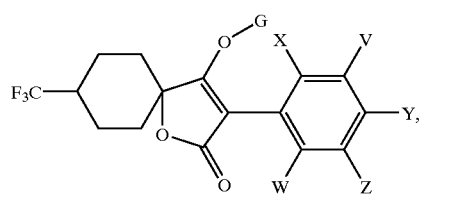
(I-2)

in which

G, V, W, X, Y and Z have the meaning given above.

Including the various meanings (a), (b), (c), (d), (e), (f) and (g) of the group G, the following principal structures (I-1-a) to (I-1-g) result if Het represents the group (1):

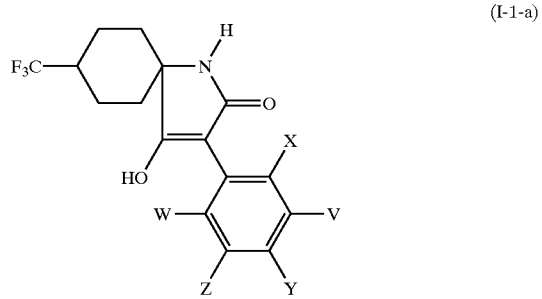
(I-1-a)

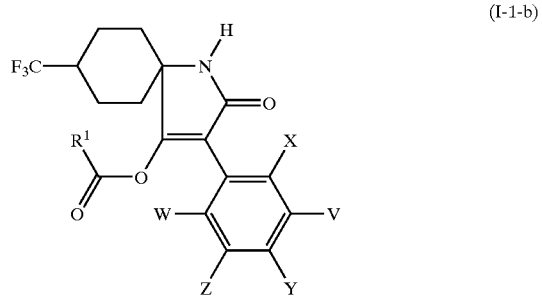
(I-1-b)

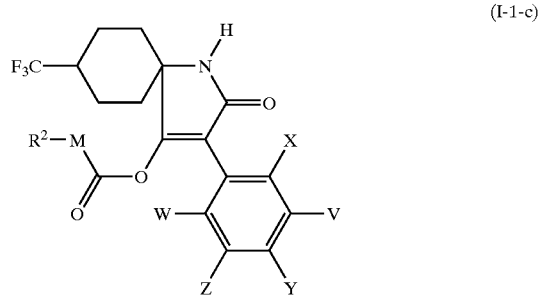
(I-1-c)

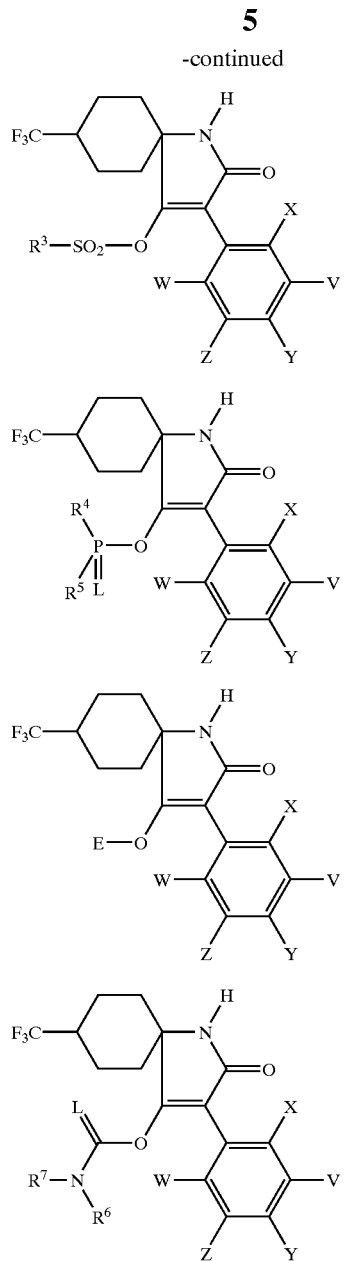
in which
E, L, M, V, W, X, Y, Z, $R^1$, $R^2$, $R^3$, $R^4$, $R^5$, $R^6$ and $R^7$ have the meanings given above.
Including the various meanings (a), (b), (c), (d), (e), (f) and (g) of the group G, the following principal structures (I-2-a) to (I-2-g) result if Het represents the group (2):
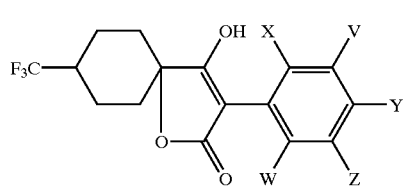
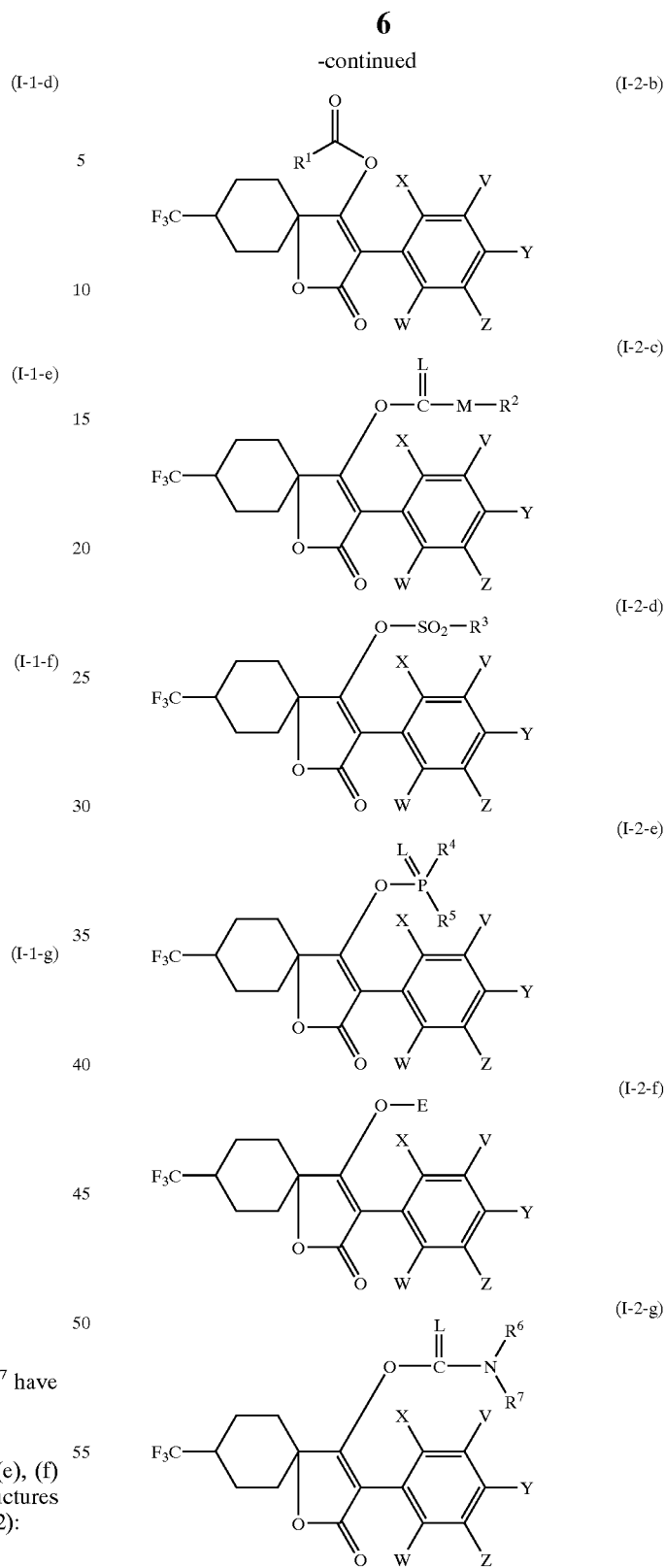
in which
E, L, M, V, W, X, Y, Z, $R^1$, $R^2$, $R^3$, $R^4$, $R^5$, $R^6$ and $R^7$ have the meaning given above.

Further more, it has been found that the novel compounds of the formula (1) are obtained by the processes described below:

(A) Compounds of the formula (I-1-a)

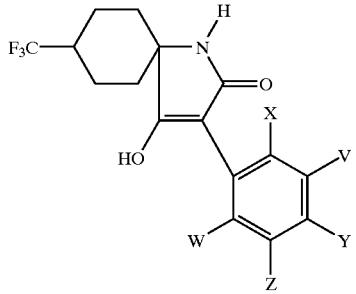

(I-1-a)

in which

V, W, X, Y and Z have the meanings given above are obtained when compounds of the formula (II)

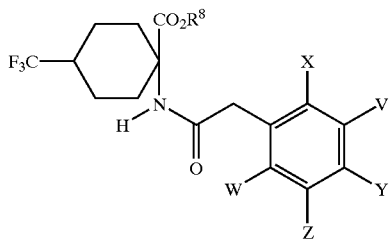

(II)

in which

V, W, X, Y and Z have the meanings given above, and $R^8$ represents alkyl (preferably $C_1$-$C_6$-alkyl)

are condensed intramolecularly in the presence of a diluent and in the presence of a base.

(B) Furthermore, it has been found that compounds of the formula (I-2-a)

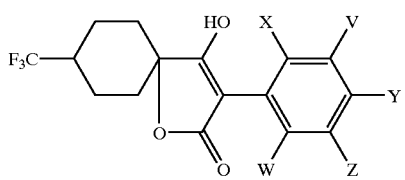

(I-2-a)

in which

V, W, X, Y and Z have the meanings given above are obtained when compounds of the formula (III)

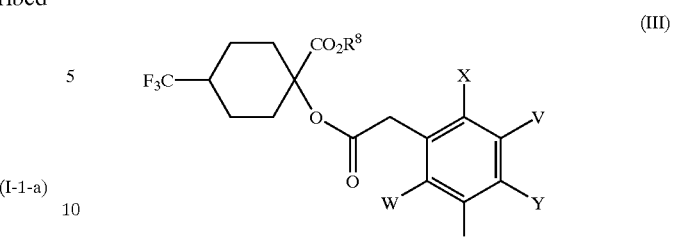

(III)

in which

V, W, X, Y, Z and $R^8$ have the meanings given above are condensed intramolecularly in the presence of a diluent and in the presence of a base.

Moreover, it has been found (C) that the compounds of the formulae (I-1-b) to (I-2-b) shown above in which $R^1$, V, W, X, Y and Z have the meanings given above are obtained when compounds of the formulae (I-1-a) to (I-2-a) shown above in which V, W, X, Y and Z have the meanings given above are in each case α) reacted with compounds of the formula (IV)

(IV)

in which $R^1$ has the meaning given above and

Hal represents halogen (in particular chlorine or bromine)

or

β) reacted with carboxylic anhydrides of the formula (V)

$R^1$—CO—O—CO—$R^1$ (V)

in which $R^1$ has the meaning given above, if appropriate in the presence of a diluent and if appropriate in the presence of an acid binder;

(D) that the compounds of the formulae (I-1-c) to (I-2-c) shown above in which $R^2$, V, W, M, X, Y and Z have the meanings given above and L represents oxygen are obtained when compounds of the formulae (I-1-a) to (I-2-a) shown above in which V, W, X, Y and Z have the meanings given above are in each case reacted with chloroformic esters or chloroformic thioesters of the formula (VI)

$R^2$—M—CO—Cl (VI)

in which $R^2$ and M have the meanings given above, if appropriate in the presence of a diluent and if appropriate in the presence of an acid binder;

(E) that compounds of the formulae (I-1-c) to (I-2-c) shown above in which $R^2$, V, W, M, X, Y and Z have the meanings given above and L represents sulphur are obtained when compounds of the formulae (I-1-a) to (I-2-a) shown above in which V, W, X, Y and Z have the meanings given above are in each case reacted with chloromonothioformic esters or chlorodithioformic esters of the formula (VU)

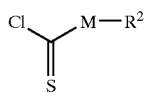 (VII)

in which

M and $R^2$ have the meanings given above, if appropriate in the presence of a diluent and if appropriate in the presence of an acid binder, (F) that compounds of the formulae (I-1-d) to (I-2-d) shown above in which $R^3$, V, W, X, Y and Z have the meanings given above are obtained when compounds of the formulae (I-1-a) to (I-2-a) shown above in which V, W, X, Y and Z have the meanings given above are in each case reacted with sulphonyl chlorides of the formula (VIII)

$R^3\text{—}SO_2\text{—}Cl$ (VIII)

in which $R^3$ has the meaning given above, if appropriate in the presence of a diluent and if appropriate in the presence of an acid binder, (G) that compounds of the formulae (I-1-e) to (I-2-e) shown above in which L, $R^4$, $R^5$, V, W, X, Y and Z have the meanings given above are obtained when compounds of the formulae (I-1-a) to (I-2-a) in which V, W, X, Y and Z have the meanings given above are in each case reacted with phosphorus compounds of the formula (IX)

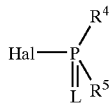 (IX)

in which

L, $R^4$ and $R^5$ have the meanings given above and

Hal represents halogen (in particular chlorine or bromine), if appropriate in the presence of a diluent and if appropriate in the presence of an acid binder, (H) that compounds of the formulae (I-1-f) to (I-2-f) shown above in which E, V, W, X, Y and Z have the meanings given above are obtained when compounds of the formulae (I-1-a) to (I-2-a) in which V, W, X, Y and Z have the meanings given above are in each case reacted with metal compounds or amines of the formulae (X) or (XI)

$Me(OR^{10})_t$ (X)

in which

Me represents a mono- or divalent metal (preferably an alkali or alkaline earth metal such as lithium, sodium, potassium, magnesium or calcium), t represents the number 1 or 2 and $R^{10}$, $R^{11}$, $R^{12}$ independently of one another represent hydrogen or alkyl (preferably $C_1$–$C_8$-alkyl), if appropriate in the presence of a diluent, (I) that compounds of the formulae (I-1-g) to (I-2-g) shown above in which L, $R^6$, $R^7$, V, W, X, Y and Z have the meanings given above are obtained when compounds of the formulae (I-1-a) to (I-2-a) shown above in which V, W, X, Y and Z have the meanings given above are in each case α) reacted with isocyanates orisothiocyanates of the formula (XII)

$R^6\text{—}N\text{=}C\text{=}L$ (XII)

in which $R^6$ and L have the meanings given above, if appropriate in the presence of a diluent and if appropriate in the presence of a catalyst or β) reacted with carbamoyl chlorides or thiocarbamoyl chlorides of the formula (XIII)

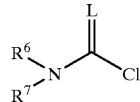 (XIII)

in which

L, $R^6$ and $R^7$ have the meanings given above, if appropriate in the presence of a diluent and if appropriate in the presence of an acid binder.

Furthermore, it has been found that the novel compounds of the formula (I) have very good activity as pesticides, preferably as insecticides, acaricides and herbicides, and are additionally frequently highly compatible with plants, in particular with crop plants.

The formula (I) provides a general definition of the compounds according to the invention. Preferred substituents or ranges of the radicals listed in the formulae mentioned hereinabove and hereinbelow are illustrated below:

V preferably represents hydrogen, halogen, $C_1$–$C_6$-alkyl or $C_1$–$C_6$-alkoxy.

W preferably represents hydrogen, nitro, cyano, halogen, $C_1$–$C_6$-alkyl, $C_2$–$C_6$-alkenyl or $C_2$–$C_6$-alkinyl, $C_1$–$C_6$-alkoxy, $C_1$–$C_4$-halogenoalkyl, $C_1$–$C_4$-halogenoalkoxy or in each case optionally halogen-, $C_1$–$C_6$-alkyl-, $C_1$–$C_6$-alkoxy-, $C_1$–$C_4$-halogenoalkyl-, $C_1$–$C_4$-halogenoalkoxy-, nitro- or cyano-substituted phenyl, phenoxy, phenylthio, phenyl-$C_1$–$C_4$-alkoxy or phenyl-$C_1$–$C_4$-alkylthio.

X preferably represents halogen, $C_1$–$C_6$-alkyl, $C_2$–$C_6$-alkenyl, $C_2$–$C_6$-alkinyl, $C_1$–$C_6$-alkoxy, $C_1$–$C_4$-halogenoalkyl, $C_1$–$C_4$-halogenoalkoxy, cyano, nitro or in each case optionally halogen-, $C_1$–$C_6$-alkyl-, $C_1$–$C_6$-alkoxy-, $C_1$–$C_4$-halogenoalkyl-, $C_1$–$C_4$-halogenoalkoxy-, nitro- or cyano-substituted phenyl, phenoxy, phenylthio, phenyl-$C_1$–$C_4$-alkoxy or phenyl-$C_1$–$C_4$-alkylthio.

Y preferably represents hydrogen, halogen, $C_1$–$C_6$-alkyl, $C_1$–$C_6$-alkoxy, $C_1$–$C_4$-halogenoalkyl, $C_1$–$C_4$-halogenoalkoxy, cyano or nitro.

Z preferably represents hydrogen, halogen, $C_1$–$C_6$-alkyl, $C_1$–$C_6$-alkoxy, $C_1$–$C_4$-halogenoalkyl, $C_1$–$C_4$-halogenoalkoxy, hydroxyl, cyano, nitro or in each case optionally halogen-, $C_1$–$C_4$-alkyl-, $C_1$–$C_4$-alkoxy-, $C_1$–$C_4$-halogenoalkyl-, $C_1$–$C_4$-halogenoalkoxy-, nitro- or cyano-substituted phenoxy, phenylthio, thiazolyloxy, pyridinyloxy, pyrimidyloxy, pyrazolyloxy, phenyl-$C_1$–$C_4$-alkyloxy or phenyl-$C_1$–$C_4$-alkylthio, or Het preferably represents one of the groups

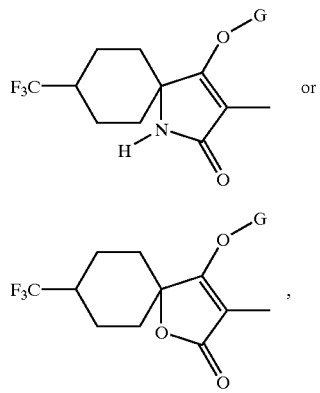

G preferably represents hydrogen (a) or represents one of the groups

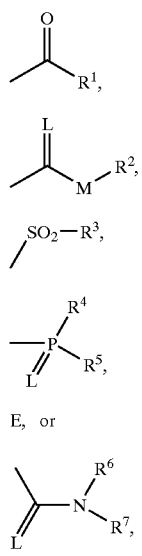

in which
  E represents a metal ion or an ammonium ion,
  L represents oxygen or sulphur and
  M represents oxygen or sulphur.

$R^1$ preferably represents in each case optionally halogen- or cyano-substituted $C_1$–$C_{20}$-alkyl, $C_2$–$C_{20}$-alkenyl, $C_1$–$C_8$-alkoxy-$C_1$–$C_8$-alkyl, $C_1$–$C_8$-alkylthio-$C_1$–$C_8$-alkyl or poly-$C_1$–$C_8$-alkoxy-$C_1$–$C_8$-alkyl or represents optionally halogen-, $C_1$–$C_6$-alkyl- or $C_1$–$C_6$-alkoxy-substituted $C_3$–$C_8$-cycloalkyl in which optionally one or two not directly adjacent methylene groups are replaced by oxygen and/or sulphur, represents optionally halogen-, cyano-, nitro-, $C_1$–$C_6$-alkyl-, $C_1$–$C_6$-alkoxy-, $C_1$–$C_6$-halogenoalkyl-, $C_1$–$C_6$-halogenoalkoxy-, $C_1$–$C_6$-alkylthio- or $C_1$–$C_6$-alkylsulphonyl-substituted phenyl, represents optionally halogen-, nitro-, cyano-, $C_1$–$C_6$-alkyl-, $C_1$–$C_6$-alkoxy-, $C_1$–$C_6$-halogenoalkyl- or $C_1$–$C_6$-halogenoalkoxy-substituted phenyl-$C_1$–$C_6$-alkyl, represents optionally halogen- or $C_1$–$C_6$-alkyl-substituted 5- or 6-membered hetaryl having one or two heteroatoms from the group consisting of oxygen, sulphur and nitrogen, represents optionally halogen- or $C_1$–$C_6$-alkyl-substituted phenoxy-$C_1$–$C_6$-alkyl or represents optionally halogen-, amino- or $C_1$–$C_6$-alkyl-substituted 5- or 6-membered hetaryloxy-$C_1$–$C_6$-alkyl having one or two heteroatoms from the group consisting of oxygen, sulphur and nitrogen.

$R^2$ represents in each case optionally halogen- or cyano-substituted $C_1$–$C_{20}$-alkyl, $C_2$–$C_{20}$-alkenyl, $C_1$–$C_8$-alkoxy-$C_2$–$C_8$-alkyl or poly-$C_1$–$C_8$-alkoxy-$C_2$–$C_8$-alkyl, represents optionally halogen-, $C_1$–$C_6$-alkyl- or $C_1$–$C_6$-alkoxy-substituted $C_3$–$C_8$-cycloalkyl or represents in each case optionally halogen-, cyano-, nitro-, $C_1$–$C_6$-alkyl-, $C_1$–$C_6$-alkoxy-, $C_1$–$C_6$-halogenoalkyl- or $C_1$–$C_6$-halogenoalkoxy-substituted phenyl or benzyl.

$R^3$ represents optionally halogen-substituted $C_1$–$C_8$-alkyl or in each case optionally halogen-, $C_1$–$C_6$-alkyl-, $C_1$–$C_6$-alkoxy-, $C_1$–$C_4$-halogenoalkyl-, $C_1$–$C_4$-halogenoalkoxy-, cyano- or nitro-substituted phenyl or benzyl.

$R^4$ and $R^5$ independently of one another represent in each case optionally halogen-substituted $C_1$–$C_8$-alkyl, $C_1$–$C_8$-alkoxy, $C_1$–$C_8$-alkylamino, di($C_1$–$C_8$-alkyl)amino, $C_1$–$C_8$-alkylthio or $C_3$–$C_8$-alkenylthio or represent in each case optionally halogen-, nitro-, cyano-, $C_1$–$C_4$-alkoxy-, $C_1$–$C_4$-halogenoalkoxy-, $C_1$–$C_4$-alkylthio-, $C_1$–$C_4$-halogenoalkylthio-, $C_1$–$C_4$-alkyl- or $C_1$–$C_4$-halogenoalkyl-substituted phenyl, phenoxy or phenylthio.

$R^6$ and $R^7$ independently of one another represent hydrogen, represent in each case optionally halogen- or cyano-substituted $C_1$–$C_8$-alkyl, $C_3$–$C_8$-cycloalkyl, $C_1$–$C_8$-alkoxy, $C_3$–$C_8$-alkenyl or $C_1$–$C_8$-alkoxy-$C_2$–$C_8$-alkyl, represent in each case optionally halogen-, $C_1$–$C_8$-alkyl-, $C_1$–$C_8$-halogenoalkyl- or $C_1$–$C_8$-alkoxy-substituted phenyl or benzyl or together represent an optionally $C_1$–$C_6$-alkyl-substituted $C_3$–$C_6$-alkylene radical in which optionally one methylene group is replaced by oxygen or sulphur.

V particularly preferably represents hydrogen, fluorine, chlorine, bromine, $C_1$–$C_4$-alkyl or $C_1$–$C_4$-alkoxy.

W particularly preferably represents hydrogen, fluorine, chlorine, bromine, $C_1$–$C_4$-alkyl, $C_1$–$C_4$-alkoxy, $C_1$–$C_2$-halogenoalkyl or $C_1$–$C_2$-halogenoalkoxy.

X particularly preferably represents fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, cyano or nitro.

Y particularly preferably represents hydrogen, fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, cyano or nitro.

Z particularly preferably represents hydrogen, fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, hydroxyl, cyano, nitro or in each case optionally fluorine-, chlorine-, bromine-, $C_1$–$C_4$-alkyl-, $C_1$–$C_4$-alkoxy-, $C_1$–$C_2$-halogenoalkyl-, $C_1$–$C_2$-halogenoalkoxy-, nitro- or cyano-substituted phenoxy or benzyloxy.

Het particularly preferably represents one of the groups

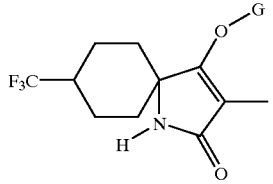 (1) or

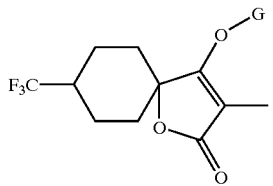 (2) ,

G particularly preferably represents hydrogen (a) or represents one of the groups

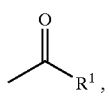 (b)

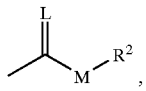 (c)

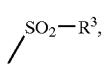 (d)

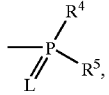 (e)

E, or (f)

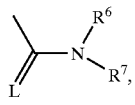 (g)

in which

E represents a metal ion or an ammonium ion,

L represents oxygen or sulphur and

M represents oxygen or sulphur.

$R^1$ particularly preferably represents in each case optionally fluorine- or chlorine-substituted $C_1$–$C_{16}$-alkyl, $C_2$–$C_{16}$-alkenyl, $C_1$–$C_6$-alkoxy-$C_1$–$C_6$-alkyl, $C_1$–$C_6$-alkylthio-$C_1$–$C_6$-alkyl or poly-$C_1$–$C_6$-alkoxy-$C_1$–$C_6$-alkyl or represents optionally fluorine-, chlorine-, $C_1$–$C_5$-alkyl- or $C_1$–$C_5$-alkoxy-substituted $C_3$–$C_7$-cycloalkyl in which optionally one or two not directly adjacent methylene groups are replaced by oxygen and/or sulphur, represents optionally fluorine-, chlorine-, bromine-, cyano-, nitro-, $C_1$–$C_4$-alkyl-, $C_1$–$C_4$-alkoxy-, $C_1$–$C_3$-halogenoalkyl-, $C_1$–$C_3$-halogenoalkoxy-, $C_1$–$C_4$-alkylthio- or $C_1$–$C_4$-alkylsulphonyl-subslituted phenyl, represents optionally fluorine-, chlorine-, bromine-, $C_1$–$C_4$-alkyl-, $C_1$–$C_4$-alkoxy-, $C_1$–$C_3$-halogenoalkyl- or $C_1$–$C_3$-halogenoalkoxy-substituted phenyl-$C_1$–$C_4$-alkyl, represents in each case optionally fluorine-, chlorine-, bromine- or $C_1$–$C_4$-alkyl-substituted pyrazolyl, thiazolyl, pyridyl, pyrimidyl, furanyl or thienyl, represents optionally fluorine-, chlorine-, bromine- or $C_1$–$C_4$-alkyl-substituted phenoxy-$C_1$–$C_5$-alkyl or represents in each case optionally fluorine-, chlorine-, bromine-, amino- or $C_1$–$C_4$-alkyl-substituted pyridyloxy-$C_1$–$C_5$-alkyl, pyrimidyloxy-$C_1$–$C_5$-alkyl or thiazolyloxy-$C_1$–$C_5$-alkyl.

$R^2$ particularly preferably represents in each case optionally fluorine- or chlorine-substituted $C_1$–$C_{16}$-alkyl, $C_2$–$C_{16}$-alkenyl, $C_1$–$C_6$-alkoxy-$C_2$–$C_6$-alkyl or poly-$C_1$–$C_6$-alkoxy-$C_2$–$C_6$-alkyl, represents optionally fluorine-, chlorine-, $C_1$–$C_4$-alkyl- or $C_1$–$C_4$-alkoxy-substituted $C_3$–$C_7$-cycloalkyl or represents in each case optionally fluorine-, chlorine-, bromine-, cyano-, nitro-, $C_1$–$C_4$-alkyl-, $C_1$–$C_3$-alkoxy-, $C_1$–$C_3$-halogenoalkyl- or $C_1$–$C_3$-halogenoalkoxy-substituted phenyl or benzyl.

$R^3$ particularly preferably represents optionally fluorine- or chlorine-substituted $C_1$–$C_6$-alkyl or in each case optionally fluorine-, chlorine-, bromine-, $C_1$–$C_4$-alkyl-, $C_1$–$C_4$-alkoxy-, $C_1$–$C_2$-halogenoalkoxy-, $C_1$–$C_2$-halogenoalkyl-, cyano- or nitro-substituted phenyl or benzyl.

$R^4$ and $R^5$ independently of one another represent in each case optionally fluorine- or chlorine-substituted $C_1$–$C_6$-alkyl, $C_1$–$C_6$-alkoxy, $C_1$–$C_6$-alkylamino, di($C_1$–$C_6$-alkyl)amino, $C_1$–$C_6$-alkylthio or $C_3$–$C_4$-alkenylthio or represent in each case optionally fluorine-, chlorine-, bromine-, nitro-, cyano-, $C_1$–$C_3$-alkoxy-, $C_1$–$C_3$-halogenoalkoxy-, $C_1$–$C_3$-alkylthio-, $C_1$–$C_3$-halogenoalkylthio-, $C_1$–$C_3$-alkyl- or $C_1$–$C_3$-halogenoalkyl-substituted phenyl, phenoxy or phenylthio.

$R^6$ and $R^7$ independently of one another represent hydrogen, represent in each case optionally fluorine- or chlorine-substituted $C_1$–$C_6$-alkyl, $C_3$–$C_6$-cycloalkyl, $C_1$–$C_6$-alkoxy, $C_3$–$C_6$-alkenyl or $C_1$–$C_6$-alkoxy-$C_2$–$C_6$-alkyl, represent in each case optionally fluorine-, chlorine-, bromine-, $C_1$–$C_5$-halogenoalkyl-, $C_1$–$C_5$-alkyl- or $C_1$–$C_5$-alkoxy-substituted phenyl or benzyl, or together represent an optionally $C_1$–$C_4$-alkyl-substituted $C_3$–$C_6$-alkylene radical in which optionally one methylene group is replaced by oxygen or sulphur.

V very particularly preferably represents hydrogen, fluorine, chlorine, bromine, methyl, ethyl, methoxy or ethoxy.

W very particularly preferably represents hydrogen, fluorine, chlorine, bromine, methyl, ethyl, propyl, methoxy or ethoxy.

X very particularly preferably represents fluorine, chlorine, bromine, methyl, ethyl, propyl, isopropyl, methoxy, ethoxy, propoxy, isopropoxy, trifluoromethyl, trifluoromethoxy, difluoromethoxy or cyano.

Y very particularly preferably represents hydrogen, fluorine, chlorine, bromine, methyl, ethyl, propyl, isopropyl, tert-butyl, methoxy, ethoxy, propoxy, isopropoxy, trifluoromethyl, trifluoromethoxy, difluoromethoxy, cyano or nitro.

Z very particularly preferably represents hydrogen, fluorine, chlorine, bromine, methyl, ethyl, propyl, isopropyl, tert-butyl, methoxy, ethoxy, propoxy, isopropoxy, trifluoromethyl, trifluoromethoxy, difluoromethoxy, cyano or nitro.

Het very particularly preferably represents one of the groups

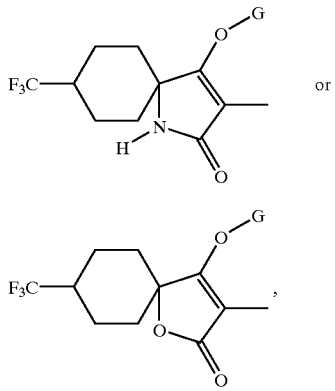

(1)

(2)

G very particularly preferably represents hydrogen (a) or represents one of the groups

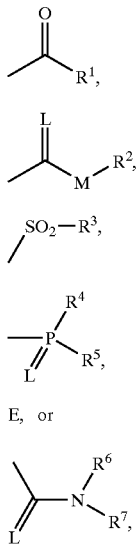

(b)

(c)

(d)

(e)

E, or (f)

(g)

in which
E represents a metal ion or an ammonium ion,
L represents oxygen or sulphur and
M represents oxygen or sulphur.
$R^1$ very particularly preferably represents in each case optionally fluorine- or chlorine-substituted $C_1$–$C_{14}$-alkyl, $C_2$–$C_{14}$-alkenyl, $C_1$–$C_4$-alkoxy-$C_1$–$C_6$-alkyl, $C_1$–$C_4$-alkylthio-$C_1$–$C_6$-alkyl, poly-$C_1$–$C_4$-alkoxy-$C_1$–$C_4$-alkyl or
represents optionally fluorine-, chlorine-, methyl-, ethyl-, n-propyl-, isopropyl-, n-butyl-, isobutyl-, tert-butyl-, methoxy-, ethoxy-, n-propoxy- or isopropoxy-substituted $C_3$–$C_6$-cycloalkyl in which optionally one or two not directly adjacent methylene groups are replaced by oxygen and/or sulphur,
represents optionally fluorine-, chlorine-, bromine-, cyano-, nitro-, methyl-, ethyl-, n-propyl-, isopropyl-, methoxy-, ethoxy-, trifluoromethyl-, trifluoromethoxy-, methylthio-, ethylthio-, methylsulphonyl- or ethylsulphonyl-substituted phenyl,
represents optionally fluorine-, chlorine-, bromine-, methyl-, ethyl-, n-propyl-, isopropyl-, methoxy-, ethoxy-, trifluoromethyl- or trifluoromethoxy-substituted benzyl,
represents in each case optionally fluorine-, chlorine-, bromine-, methyl- or ethyl-substituted furanyl, thienyl or pyridyl,
represents optionally fluorine-, chlorine-, methyl- or ethyl-substituted phenoxy-$C_1$–$C_4$-alkyl or
represents in each case optionally fluorine-, chlorine-, amino-, methyl- or ethyl-substituted pyridyloxy-$C_1$–$C_4$-alkyl, pyrimidyloxy-$C_1$–$C_4$-alkyl or thiazolyloxy-$C_1$–$C_4$-alkyl.
$R^2$ very particularly preferably represents in each case optionally fluorine- or chlorine-substituted $C_1$–$C_{14}$-alkyl, $C_2$–$C_{14}$-alkenyl, $C_1$–$C_4$-alkoxy-$C_2$–$C_6$-alkyl or poly-$C_1$–$C_4$-alkoxy-$C_2$–$C_6$-alkyl,
represents optionally fluorine-, chlorine-, methyl-, ethyl-, n-propyl-, isopropyl- or methoxy-substituted $C_3$–$C_6$-cycloalkyl, or represents in each case optionally fluorine-, chlorine-, cyano-, nitro-, methyl-, ethyl-, n-propyl-, isopropyl-, methoxy-, ethoxy-, trifluoromethyl- or trifluoromethoxy-substituted phenyl or benzyl.
$R^3$ very particularly preferably represents in each case optionally fluorine- or chlorine-substituted methyl, ethyl, propyl, isopropyl, butyl, tert-butyl, or in each case optionally fluorine-, chlorine-, bromine-, methyl-, ethyl-, isopropyl-, tert-butyl-, methoxy-, ethoxy-, isopropoxy-, trifluoromethyl-, trifluoromethoxy-, cyano- or nitro-substituted phenyl or benzyl.
$R^4$ and $R^5$ independently of one another very particularly preferably represent in each case optionally fluorine- or chlorine-substituted $C_1$–$C_4$-alkyl, $C_1$–$C_4$alkoxy, $C_1$–$C_4$-alkylamino, di-($C_1$–$C_4$-alkyl)amino or $C_1$–$C_4$-alkylthio or represent in each case optionally fluorine-, chlorine-, bromine-, nitro-, cyano-, methyl-, methoxy-, trifluoromethyl- or trifluoromethoxy-substituted phenyl, phenoxy or phenylthio.
$R^6$ and $R^7$ independently of one another very particularly preferably represent hydrogen, represent in each case optionally fluorine- or chlorine-substituted $C_1$–$C_4$-alkyl, $C_3$–$C_6$-cycloalkyl, $C_1$–$C_4$-alkoxy, $C_3$–$C_4$-alkenyl or $C_1$–$C_4$-alkoxy-$C_2$–$C_4$-alkyl, represent in each case optionally fluorine-, chlorine-, bromine-, methyl-, methoxy- or trifluoromethyl-substituted phenyl or benzyl, or together represent an optionally methyl- or ethyl-substituted $C_5$–$C_6$-alkylene radical in which optionally one methylene group is replaced by oxygen or sulphur.

The abovementioned general or preferred radical definitions or illustrations can be combined with each other as desired, i.e. including combinations between the respective ranges and preferred ranges. They apply both to the end products and, correspondingly, to the precursors and intermediates.

Preference according to the invention is given to the compounds of the formula (I) which contain a combination of the meanings listed above as being preferred (preferable).

Particular preference according to the invention is given to the compounds of the formula (I) which contain a combination of the meanings listed above as being particularly preferred.

Very particular preference according to the invention is given to the compounds of the formula (I) which contain a combination of the meanings listed above as being very particularly preferred.

Saturated or unsaturated hydrocarbon radicals such as alkyl or alkenyl may in each case be straight-chain or branched as far as this is possible, including in combination with heteroatoms, such as, for example, in alkoxy.

Optionally substituted radicals may be mono- or polysubstituted and, in the case of polysubstitutions, the substituents may be identical or different.

Besides the compounds mentioned in the Preparation Examples, the following compounds of the formula (I-1-a) may be specifically mentioned:

TABLE 1

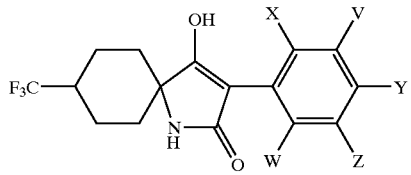

(I-1-a)

| V | X | W | Y | Z |
|---|---|---|---|---|
| H | Br | H | Cl | H |
| H | Cl | H | Br | H |
| H | Cl | H | Cl | H |
| H | Cl | H | F | H |
| H | F | H | Cl | H |
| H | Cl | H | OCH$_3$ | H |
| H | Cl | H | CH$_3$ | H |
| H | OCH$_3$ | H | Cl | H |
| H | OCH$_3$ | H | OCH$_3$ | H |
| H | CH$_3$ | H | Cl | H |
| H | CH$_3$ | H | F | H |
| H | CH$_3$ | H | OCH$_3$ | H |
| H | CH$_3$ | H | t-C$_4$H$_9$ | H |
| H | CH$_3$ | H | CH$_3$ | H |
| H | Cl | Cl | H | H |
| H | Cl | F | H | H |
| H | Cl | OCH$_3$ | H | H |
| H | Cl | CH$_3$ | H | H |
| H | Cl | OC$_2$H$_5$ | H | H |
| H | OCH$_3$ | OCH$_3$ | H | H |
| H | CH$_3$ | CH$_3$ | H | H |
| H | Br | CH$_3$ | Br | H |
| H | Cl | Cl | CH$_3$ | H |
| H | CH$_3$ | Br | CH$_3$ | H |
| H | CH$_3$ | Cl | CH$_3$ | H |
| H | CH$_3$ | OCHF$_2$ | CH$_3$ | H |
| H | CH$_3$ | OCH$_2$CF$_3$ | CH$_3$ | H |
| H | CH$_3$ | OC$_2$H$_5$ | CH$_3$ | H |
| H | CH$_3$ | OCH$_3$ | CH$_3$ | H |
| H | CH$_3$ | CH$_3$ | CH$_3$ | H |
| H | Br | Br | CH$_3$ | H |
| H | Cl | Cl | CH$_3$ | H |
| H | C$_2$H$_5$ | C$_2$H$_5$ | Br | H |
| H | CH$_3$ | CH$_3$ | Br | H |
| H | CH$_3$ | CH$_3$ | OCH$_3$ | H |
| H | Br | Cl | CH$_3$ | H |
| H | Br | CH$_3$ | Cl | H |
| H | Cl | CH$_3$ | Br | H |
| H | C$_2$H$_5$ | Br | CH$_3$ | H |
| H | CH$_3$ | O—C$_3$H$_7$ | CH$_3$ | H |
| H | CH$_3$ | CH$_3$ | Cl | H |
| H | Cl | H | Cl | Cl |
| H | CH$_3$ | H | CH$_3$ | CH$_3$ |
| H | CH$_3$ | H | Cl | CH$_3$ |
| H | Br | H | Cl | CH$_3$ |
| H | Br | H | CH$_3$ | CH$_3$ |
| H | Cl | H | Br | CH$_3$ |
| H | Cl | H | Cl | CH$_3$ |
| H | CH$_3$ | H | Br | CH$_3$ |
| H | Cl | H | Cl | F |
| H | Cl | H | CH$_3$ | Cl |
| H | CH$_3$ | H | H | H |
| H | Cl | H | H | H |
| H | Br | H | H | H |
| H | CF$_3$ | H | H | H |
| H | OCH$_3$ | H | H | H |
| H | CH$_3$ | CH$_3$ | CH$_3$ | CH$_3$ |
| CH$_3$ | CH$_3$ | H | CH$_3$ | CH$_3$ |
| CH$_3$ | CH$_3$ | CH$_3$ | H | CH$_3$ |

TABLE 1-continued

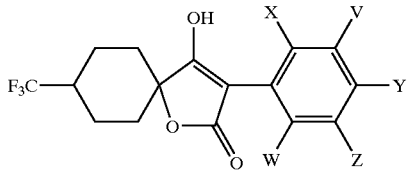

(I-1-a)

| V | X | W | Y | Z |
|---|---|---|---|---|
| H | CH$_3$ | CH$_3$ | CH$_3$ | F |
| H | CH$_3$ | CH$_3$ | CH$_3$ | Cl |
| H | CH$_3$ | CH$_3$ | CH$_3$ | Br |
| H | CH$_3$ | CH$_3$ | H | Cl |
| H | CH$_3$ | CH$_3$ | H | Br |
| H | Cl | Cl | H | Br |
| CH$_3$ | CH$_3$ | CH$_3$ | CH$_3$ | CH$_3$ |

Besides the compounds mentioned in the Preparation Examples, the following compounds of the formula (I-2-a) may be specifically mentioned:

TABLE 2

(I-2-a)

in which

V, W, X, Y and Z have the meanings given in Table 1.

Using, in accordance with process (A), ethyl N-[(4-chloro-2,6-dimethyl)-phenylacetyl]-1-amino-4-trifluoromethyl-cyclohexanecarboxylate as starting material, the course of the process according to the invention can be represented by the following equation:

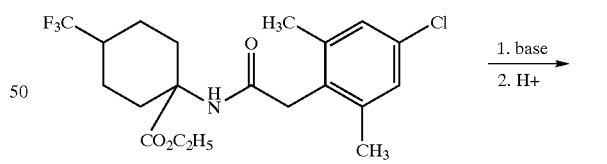

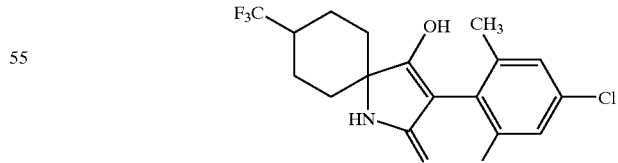

Using, in accordance with process (B), ethyl 0-[(2-chloro-6-methyl)-phenylacetyl]-1-hydroxy-4-trifluoromethyl-cyclohexanecarboxylate, the course of the process according to the invention can be represented by the following equation:

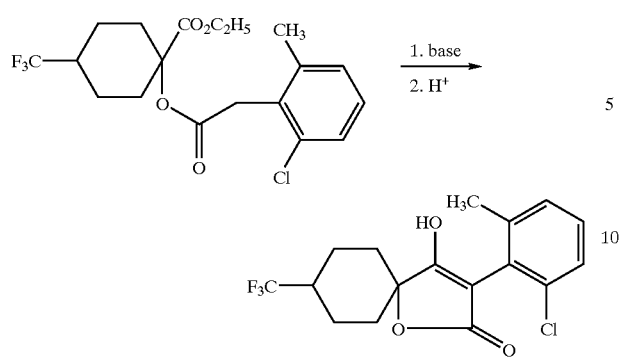

Using, in accordance with process (Cat), 3-[(2-chloro-4-methyl)-phenyl]-5,5-(3-trifluoromethyl-pentamethylenediyl)-pyrrolidine-2,4-dione and pivaloyl chloride as starting materials, the course of the process according to the invention can be represented by the following equation:

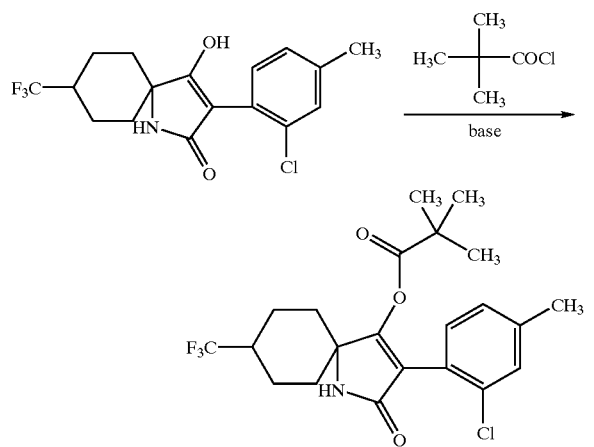

Using, in accordance with process (C) (variante β), 3-[(2,4-dichloro)-phenyl]-4-hydroxy-5,5-(3-trifluoromethyl-pentamethylenediyl)-$\Delta^3$-dihydrofuran-2-one and acetic anhydride as starting materials, the course of the process according to the invention can be represented by the following equation:

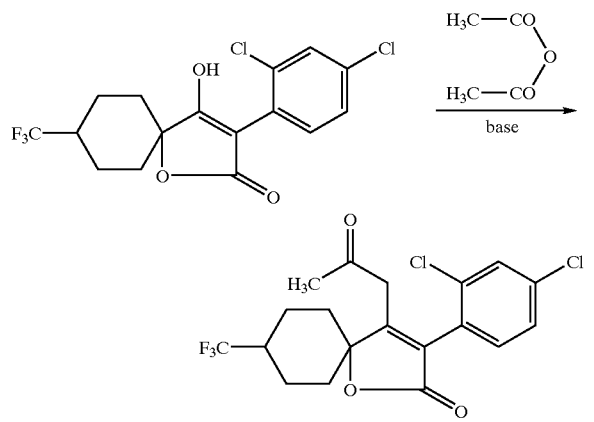

Using, in accordance with process (D), 8-[(2,4-dichloro)-phenyl]-5,5-(3-trifluoromethyl-pentamethylenediyl)-pyrrolidine-2,4-dione and ethoxyethyl chloroformate as starting materials, the course of the process according to the invention can be represented by the following equation:

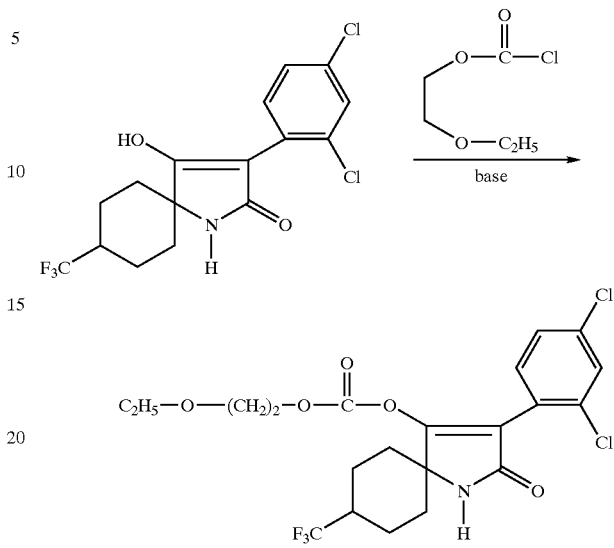

Using, in accordance with process (E), 3-[(2,6-dibromo4-methyl)-phenyl]4-hydroxy-5,5-(3-tri fluoromethyl-pentamethylenediyl)-$\Delta^3$-dihydrofuran-2-one and methyl chloromonothioformate as starting materials, the course of the process according to the invention can be represented as follows:

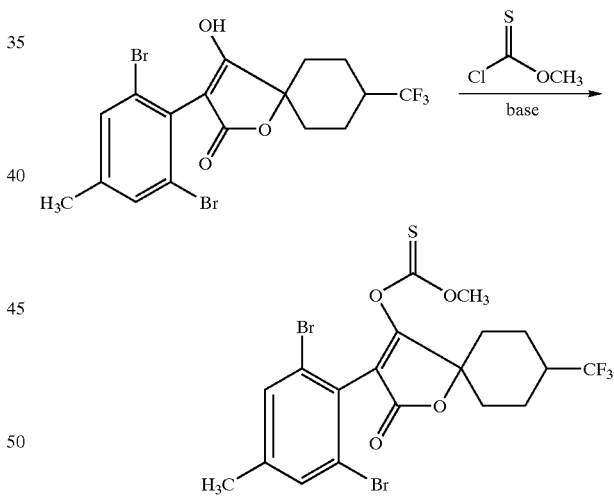

Using, in accordance with process (F), 2-[(2,4,6-trimethyl)-phenyl]-5,5-(3-trifluoromethyl-pentamethylenediyl)-pyrrolidine-2,4-dione and methanesulphonyl chloride as starting materials, the course of the reaction can be represented by the following equation:

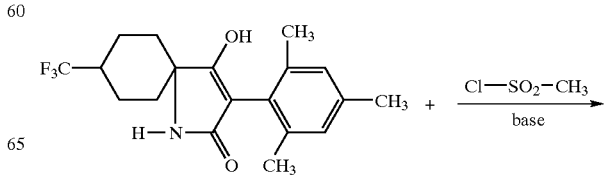

-continued

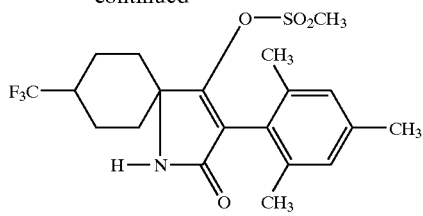

Using, in accordance with process (G), 2-[(4-bromo-2-chloro-6-methyl)-phenyl]-4-hydroxy-5,5-(3-trifluoromethyl-pentamethylenediyl)-Δ³-dihydrofuran-2-one and 2,2,2-trifluoroethyl methanethio-phosphonyl chloride as starting materials, the course of the reaction can be represented by the following equation:

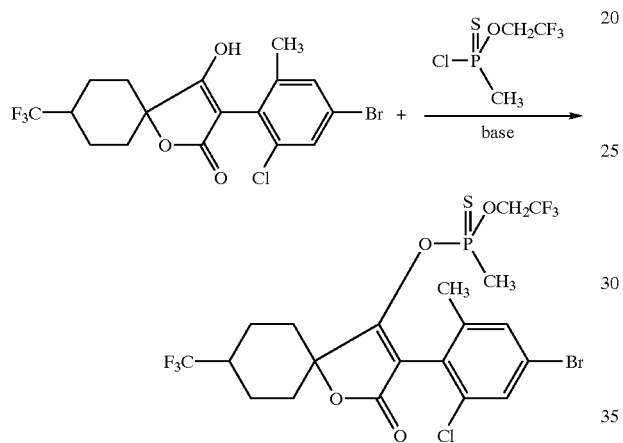

Using, in accordance with process (H), 3-[(2,4-dichloro)₆-methylphenyl]-5,5-(3-trifluoromethyl-pentamethylenediyl)-pyrrolidine-2,4-dione and NaOH as components, the course of the process according to the invention can be represented by the following equation:

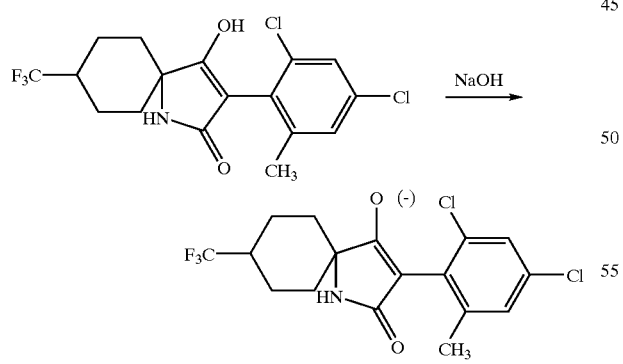

Using, in accordance with process (I) (variant a), 3-[(2-chloro-4-bromo-5-methyl)-phenyl]4-hydroxy-5,5-(3-trifluoromethyl-pentamethylenediyl)-3-dihydrofuran-2-one and ethyl isocyanate as starting materials, the course of the reaction can be represented by the following reaction scheme:

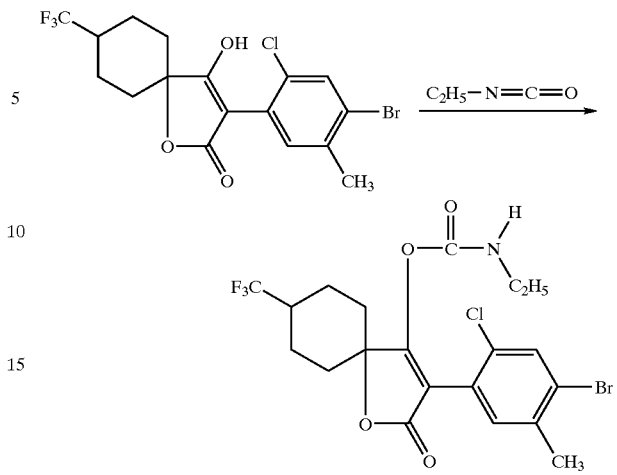

Using, in accordance with process (I) (variante β), 3-[(2-chloro-4,6-dimethyl)-phenyl]-5,5-(3-trifluoromethyl-pentamethylenediyl)-pyrrolidine-2,4-dione and dimethyl-carbamoyl chloride as starting materials, the course of the reaction can be represented by the following scheme:

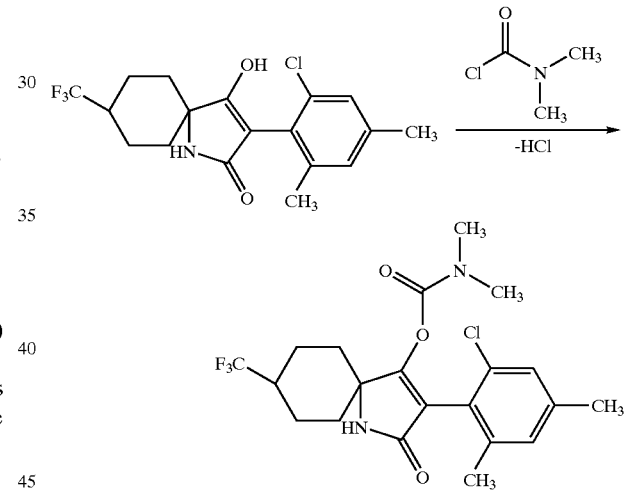

The compounds of the formula (II)

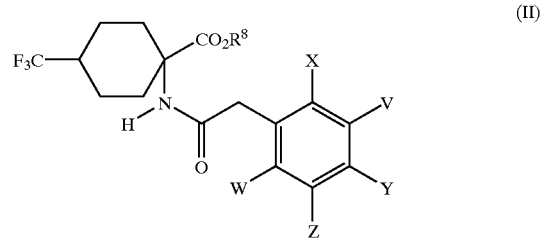

in which

V, W, X, Y, Z and R⁸ have the meanings given above, required as starting materials in the process (A) according to the invention are novel.

The acylamino acid esters of the formula (II) are obtained, for example, when amino acid derivatives of the formula (XIV)

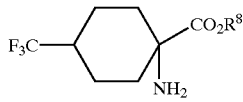
(XIV)

in which
R⁸ has the meaning given above
are acylated with substituted phenylacetyl halides of the formula (XV)

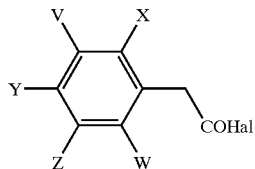
(XV)

in which
V, W, X, Y and Z have the meanings given above and
Hal represents chlorine or bromine
(Chem. Reviews 52, 237–416 (1953); Bhattacharya, Indian J. Chem. 6, 341–5, 1968)
or when acylamino acids of the formula (XVI)

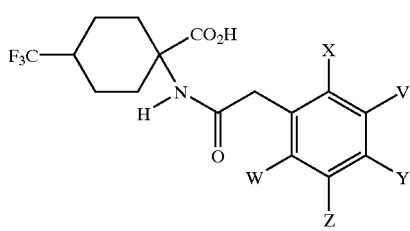
(XVI)

in which
V, W, X, Y and Z have the meanings given above
are esterified (Chem. Ind. (London) 1568 (1968)).

The compounds of the formula (XVI)

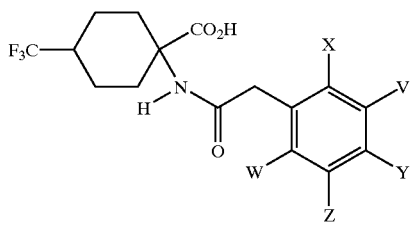
(XVI)

in which
V, W, X, Y and Z have the meanings given above
are novel.

The compounds of the formula (XVI) are obtained, for example, when 1-amino-4-trifluoromethyl-cyclohexane-carboxylic acid of the formula (XVII)

(XVII)

is acylated with substituted phenylacetyl halides of the formula (XV)

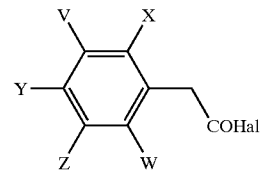
(XV)

in which

V, W, X, Y and Z have the meanings given above and

Hal represents chlorine or bromine according to Schotten-Baumann (Organikum, VEB Deutscher Verlag der Wissen-schaften, Berlin 1977, p. 505).

The compounds of the formula (XV) are known and can be prepared by the known processes of the laid-open patents cited at the outset.

The compounds of the formulae (XIV) and (XVII) are novel and can be prepared by known processes (see, for example, Compagnon, Ann. Chim. (Paris) [14] 5, p. 11–22, 23–27 (1970), L. Munday, J. Chem. Soc. 4372 (1961); J. T. Eward, C. Jitrangeri, Can. J. Chem. 53, 3339 (1975).

The I-amino4-trifluoromethyl-cyclohexane-carboxylic acid (XVII) is generally obtainable by the Bucherer-Bergs synthesis or by the Strecker synthesis and is in each case obtained in different isomer forms. Thus, under the conditions of the Bucherer-Bergs synthesis, the isomer (for simplicity called β below) in which the trifluoromethyl group and the carboxyl group are equatorial is predominantly obtained, while under the conditions of the Strecker synthesis the isomer (for simplicity called a below) in which the amino group and the trifluoromethyl group are equatorial is predominantly obtained.

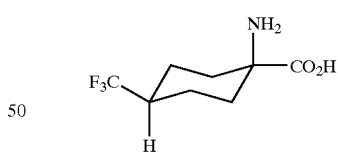

Bucherer-Bergs synthesis
(β isomer)

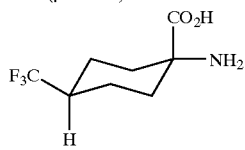

Strecker synthesis
(α isomer)

(L. Munday, J. Chem. Soc. 4372 (1961); J. T. Eward, C. Jitrangeri, Can. J. Chem. 53, 3339 (1975).

Furthermore, the starting materials of the formula (I)

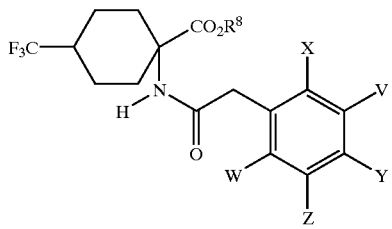
(II)

in which
V, W, X. Y, Z and $R^8$ have the meanings given above
used in the above process (A) can be prepared when
1-amino-4-trifluoromethyl-cyclohexane-carbonitrile of the formula (XVIII)

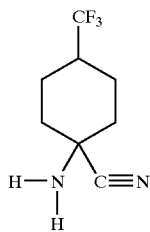
(XVIII)

is reacted with substituted phenylacetyl halides of the formula (XV)

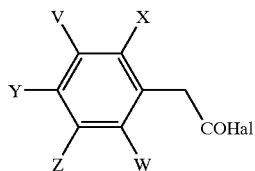
(XV)

in which
V, W, X, Y, Z and Hal have the meanings given above,
to give compounds of the formula (XIX)

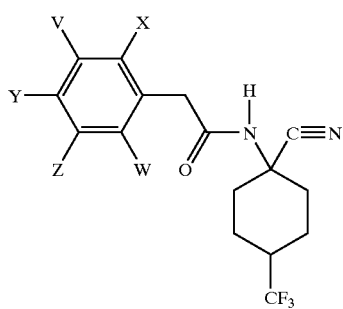
(XIX)

in which
V, W, X, Y and Z have the meanings given above
and these are subsequently subjected to acidic alcoholysis.

The compounds of the formula (XIX) are likewise novel.
The compounds of the formula (XVIII) are also novel.

The compounds of the formula (III)

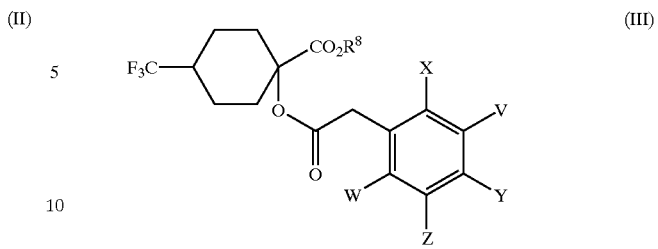
(III)

in which
V, W, X, Y, Z and $R^8$ have the meanings given above
required as starting materials in the process (B) according to the invention are novel,
except for the compound below

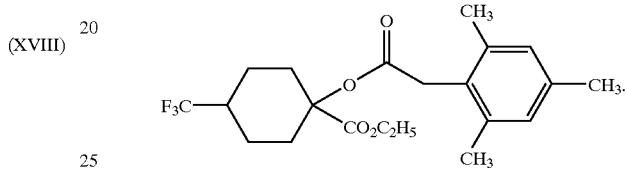

They can be prepared in a simple manner by methods known in principle.
The compounds of the formula (III), for example, are obtained when
1-hydroxy4-trifluoromethyl-cyclohexane-carboxylic esters of the formula (XX)

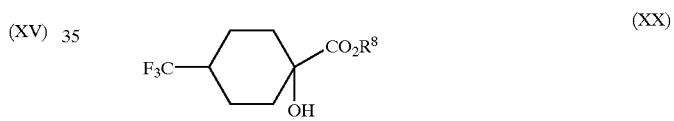
(XX)

in which
$R^8$ has the meaning given above
are acylated with substituted phenylacetyl halides of the formula (XV)

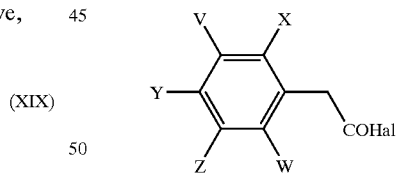

in which
V, W, X, Y, Z and Hal have the meanings given above
(Chem. Reviews 52, 237–416 (1953)).

Some of the 1-hydroxy-4-trifluoromethyl-cyclohexyl-carboxylic esters of the formula (XX) are novel. They are obtained, for example, by alcoholizing 1-hydroxy-4-trifluoromethyl-cyclohexane-carbonitrile in the presence of acids, for example according to Pinner (see Preparation Example). The cyanohydrin is obtained, for example, by reacting 4-trifluoromethyl-cyclohexan-1-one with hydrocyanic acid.

The acyl halides of the formula (IV), carboxylic anhydrides of the formula (V), chloroformic esters or chloroformic thioesters of the formula (VI), chloromonothioformic esters or chlorodithioformic esters of the formula (V[), sulphonyl chlorides of the formula (VIII), phosphorus compounds of the formula (IX) and metal hydroxides, metal alkoxides or amines of the formulae (X) and (XI) and isocyanates of the formula (XII) and carbamoyl chlorides of the formula (XIII) furthermore required as starting materials for carrying out the processes (C), (D), (E), (F), (G), (H) and (I) according to the invention are generally known compounds of organic or inorganic chemistry.

The compounds of the formula (XV) are furthermore known from the patent applications cited at the outset, and/or they can be prepared by the methods given therein.

The process (A) is characterized in that compounds of the formula (II) in which V, W, X, Y, Z and $R^8$ have the meanings given above are subjected to an intramolecular condensation in the presence of a diluent and in the presence of a base.

Suitable diluents for the process (A) according to the invention are all organic solvents which are inert to the reaction participants. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide and N-methyl-pyrrolidone, and also alcohols, such as methanol, ethanol, propanol, isopropanol, butanol, isobutanol and tert-butanol.

Suitable bases (deprotonating agents) for carrying out the process (A) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be employed in the presence of phase-transfer catalysts, such as, for example, triethylbenzylammonium chloride, tetrabutylammonium bromide, Adogen 464 (=methyltrialkyl $(C_9-C_{10})$ammonium chloride) or TDA 1 (=tris-(methoxyethoxyethyl)-amine). Alkali metals such as sodium and potassium can also be used. Furthermore, alkali metal and alkaline earth metal amides and hydrides, such as sodium amide, sodium hydride and calcium hydride, and additionally also alkali metal alkoxides, such as sodium methoxide, sodium ethoxide and potassium tert-butoxide can be employed.

When carrying out the process (A) according to the invention, the reaction temperature can be varied within a relatively wide range. In general, the reaction is carried out at temperatures between −75° C. and 200° C., preferably between −50° C. and 150° C.

The process (A) according to the invention is generally carried out under atmospheric pressure.

When carrying out the processss (A) according to the invention, the reaction component of the formula (II) and the deprotonating base are generally employed in equimolar to approximately double-equimolar amounts. However, it is also possible to use a larger excess (up to 3 mol) of one component or the other.

The process (B) is characterized in that compounds of the formula (III) in which V, W, X, Y, Z and $R^8$ have the meanings given above are condensed intramolecularly in the presence of a diluent and in the presence of a base.

Suitable diluents for the process (B) according to the invention are all organic solvents which are inert to the reaction participants. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide and N-methyl-pyrrolidone. It is also possible to employ alcohols, such as methanol, ethanol, propanol, isopropanol, butanol, isobutanol and tertbutanol.

Suitable bases (deprotonating agents) for carrying out the process (B) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be employed in the presence of phase-transfer catalysts, such as, for example, triethylbenzylammonium chloride, tetrabutylammonium bromide, Adogen 464 (=methyltrialkyl $(C_8-C_{10})$ammonium chloride) or TDA 1 (=tris-(methoxyethoxyethyl)-amine). Alkali metals such as sodium and potassium can also be used. Furthermore, alkali metal and alkaline earth metal amides and hydrides, such as sodium amide, sodium hydride and calcium hydride, and additionally also alkali metal alkoxides, such as sodium methoxide, sodium ethoxide and potassium tert-butoxide can be employed.

When carrying out the process (B) according to the invention, the reaction temperature can be varied within a relatively wide range. In general, the reaction is carried out at temperatures between −75° C. and 200° C., preferably between −50° C. and 150° C.

The process (B) according to the invention is generally carried out under atmospheric pressure.

When carrying out the process (B) according to the invention, the reaction components of the formula (III) and the deprotonating bases are generally employed in approximately equimolar amounts. However, it is also possible to use a relatively large excess (up to 3 mol) of one component or the other.

The process $(C_\alpha)$ is characterized in that compounds of the formulae (I-1-a) to (I-2-a) are in each case reacted with carbonyl halides of the formula (IV), if appropriate in the presence of a diluent and if appropriate in the presence of an acid binder.

Suitable diluents for the process $(C_\alpha)$ according to the invention are all solvents which are inert to the acyl halides. Preference is given to using hydrocarbons, such as benzine, benzene, toluene, xylene and tetraline, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, and also strongly polar solvents, such as dimethylformamide, dimethyl sulphoxide and sulpholane. The stability of the acyl halide to hydrolysis permitting, the reaction may also be carried out in the presence of water.

Suitable acid binders for the reaction according to the process (Ca) according to the invention are all customary acid acceptors. Preference is given to using tertiary amines, such as triethylamine, pyridine, diazabicyclooctane (DABCO), diazabicycloundecene (DBU), diazabicyclononene (DBN), Hünig base and N,N-dimethylaniline, furthermore alkaline earth metal oxides, such as magnesium oxide and calcium oxide, moreover alkali metal and alkaline earth metal carbonates, such as sodium carbonate, potassium carbonate and calcium carbonate, and also alkali metal hydroxides, such as sodium hydroxide and potassium hydroxide.

The reaction temperature in the process $(C_\alpha)$ according to the invention can be varied within a relatively wide range.

In general, the reaction is carried out at temperatures between −20° C. and +150° C., preferably between 0° C. and 100° C.

When carrying out the processs ($C_\alpha$) according to the invention, the starting materials of the formulae (I-1-a) to (I-2-a) and the carbonyl halide of the formula (IV) are generally in each case employed in approximately equivalent amounts. However, it is also possible to employ a relatively large excess (up to 5 mol) of the carbonyl halide. Work-up is carried out by customary methods.

The process ($C_\beta$) is characterized in that compounds of the formulae (I-1-a) to (I-2-a) are in each case reacted with carboxylic anhydrides of the formula (V), if appropriate in the presence of a diluent and if appropriate in the presence of an acid binder.

Preferred diluents for the process ($C_\beta$) according to the invention are those diluents which are also preferred when acyl halides are used. Otherwise, it is also possible for a carboxylic anhydride employed in excess to act simultaneously as diluent.

In the process ($C_\beta$), acid binders which are added, if appropriate, are preferably those acid binders which are also preferred when acyl halides are used.

In the process ($C_\beta$) according to the invention, the reaction temperature can be varied within a relatively wide range. In general, the reaction is carried out at temperatures between −20° C. and +150° C., preferably between 0° C. and 100° C.

When carrying out the processs ($C_\beta$) according to the invention, the starting materials of the formulae (I-1-a) to (I-2-a) and the carboxylic anhydride of the formula (V) are generally each employed in approximately equivalent amounts. However, it is also possible to use a relatively large excess (up to 5 mol) of the carboxylic anhydride. Work-up is carried out by customary methods.

In general, the adopted procedure is to remove diluent and excess carboxylic anhydride and also the carboxylic acid formed by distillation or by washing with an organic solvent or with water.

The process (D) is characterized in that compounds of the formulae (I-1-a) to (I-2-a) are in each case reacted with chloroformic esters or chloroformic thioesters of the formula (VI), if appropriate in the presence of a diluent and if appropriate in the presence of an acid binder.

Suitable acid binders for the process (D) according to the invention are all customary acid acceptors. Preference is given to using tertiary amines, such as triethylamine, pyridine, DABCO, DBU, DBN, Hünig base and N,N-dimethyl-aniline, furthermore alkaline earth metal oxides, such as magnesium oxide and calcium oxide, moreover alkali metal and alkaline earth metal carbonates, such as sodium carbonate, potassium carbonate and calcium carbonate, and also alkali metal hydroxides, such as sodium hydroxide and potassium hydroxide.

Suitable diluents for the process (D) according to the invention are all solvents which are inert towards the chloroformic esters or chloroformic thioesters. Preference is given to using hydrocarbons, such as benzine, benzene, toluene, xylene and tetraline, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, moreover nitriles, such as acetonitrile, and also strongly polar solvents, such as dimethylformamide, dimethyl sulphoxide and sulpholane.

When carrying out the processs (D) according to the invention, the reaction temperature can be varied within a relatively wide range. In general, the reaction temperature is between −20° C. and +100° C., preferably between 0° C. and 50° C.

The process (D) according to the invention is generally carried out under atmospheric pressure.

When carrying out the process (D) according to the invention, the starting materials of the formulae (I-1-a) to (I-2-a) and the appropriate chloroformic ester or chloroformic thioester of the formula (VI) are generally in each case employed in approximately equivalent amounts. However, it is also possible to employ a relatively large excess (up to 2 mol) of one component or the other. Work-up is carried out by customary methods. In general, precipitated salts are removed and the reaction mixture that remains is concentrated by stripping the diluent.

The process (E) according to the invention is characterized in that compounds of the formulae (I-1-a) to (I-2-a) are in each case reacted with compounds of the formula (VII) in the presence of a diluent and, if appropriate, in the presence of an acid binder.

In the preparation process (E), approximately 1 mol of chloromonothioformic ester or chlorodithioformic ester of the formula (VII) is reacted per mole of starting material of the formulae (I-1-a) to (I-2-a), at from 0 to 120° C., preferably from 20 to 60° C.

Suitable diluents which are added, if appropriate, are all inert polar organic solvents, such as ethers, amides, sulphones, sulphoxides, but also halogenoalkanes.

Preference is given to using dimethyl sulphoxide, tetrahydrofuran, dimethylformamide, ethyl acetate or methylene chloride.

If, in a preferred embodiment, the enolate salt of the compounds (I-1-a) to (I-2-a) is prepared by addition of strong deprotonating agents, such as, for example, sodium hydride or potassium tert-butoxide, it is not necessary to add further acid binders.

Suitable bases for the process (E) are all customary proton acceptors. Preference is given to using alkali metal hydrides, alkali metal alkoxides, alkali metal or alkaline earth metal carbonates or bicarbonates or nitrogen bases. Examples which may be mentioned are sodium hydride, sodium methoxide, sodium hydroxide, calcium hydroxide, potassium carbonate, sodium bicarbonate, triethylamine, dibenzylamine, diisopropylamine, pyridine, quinoline, diazabicyclooctane (DABCO), diazabicyclononene (DBN) and diazabicycloundecene (DBU).

The reaction can be carried out at atmospheric pressure or under elevated pressure and is preferably carried out at atmospheric pressure. Work-up is carried out by customary methods.

The process (F) according to the invention is characterized in that compounds of the formulae (I-1-a) to (I-2-a) are in each case reacted with sulphonyl chlorides of the formula (VIII), if appropriate in the presence of a diluent and if appropriate in the presence of an acid binder.

In the preparation process (F), approximately 1 mol of sulphonyl chloride of the formula (VIII) is reacted per mole of starting material of the formula (I-1-a) to (I-2-a), at from −20 to 150° C., preferably from 0 to 70° C.

The process (F) is preferably carried out in the presence of a diluent.

Suitable diluents are all inert polar organic solvents, such as ethers, amides, ketones, carboxylic esters, nitrites, sulphones, sulphoxides or halogenated hydrocarbons, such as methylene chloride.

Preference is given to using dimethyl sulphoxide, tetrahydrofuran, dimethylformamide, ethyl acetate or methylene chloride.

If, in a preferred embodiment, the enolate salt of the compounds (I-1-a) to (I-2-a) is prepared by addition of strong deprotonating agents (such as, for example, sodium hydride or potassium tert-butoxide), it is not necessary to add further acid binders.

If acid binders are employed, these are customary inorganic or organic bases, for example sodium hydroxide, sodium carbonate, potassium carbonate, pyridine and triethylamine.

The reaction can be carried out at atmospheric pressure or under elevated pressure and is preferably carried out at atmospheric pressure. Work-up is carried out by customary methods.

The process (G) according to the invention is characterized in that compounds of the formulae (I-1-a) to (I-2-a) are in each case reacted with phosphorus compounds of the formula (IX), if appropriate in the presence of a diluent and if appropriate in the presence of an acid binder.

In the preparation process (G), 1 to 2, preferably 1 to 1.3, mol of the phosphorus compound of the formula (IX) are reacted per mole of the compounds (I-1-a) to (I-2-a) at temperatures between 40° C. and 150° C., preferably between –10 and 110° C., to give compounds of the formulae (I-1-e) to (I-2-e).

The process (G) is preferably carried out in the presence of a diluent.

Suitable diluents are all inert polar organic solvents, such as ethers, carboxylic esters, halogenated hydrocarbons, ketones, amides, nitriles, sulphones, sulphoxides, etc.

Preference is given to using acetonitrile, dimethyl sulphoxide, tetrahydrofuran, dimethylformamide or methylene chloride.

Suitable acid binders which are added, if appropriate, are customary inorganic or organic bases such as hydroxides, carbonates or amines. Examples include sodium hydroxide, sodium carbonate, potassium carbonate, pyridine and triethylamine.

The reaction can be carried out at atmospheric pressure or under elevated pressure and is preferably carried out under atmospheric pressure. Work-up is carried out by customary methods of organic chemistry. The end products are preferably purified by crystallization, chromatographic purification or "incipient distillation", i.e. removal of the volatile components under reduced pressure.

The process (H) is characterized in that compounds of the formulae (I-1-a) to (I-2-a) are in each case reacted with metal hydroxides or metal alkoxides of the formula (X) or amines of the formula (XI), if appropriate in the presence of a dilluent.

Preferred diluents for the process (H) according to the invention are ethers, such as tetrahydrofuran, dioxane, diethyl ether, or else alcohols, such as methanol, ethanol, isopropanol, but also water.

The process (H) according to the invention is generally carried out under atmospheric pressure.

The reaction temperature is generally between –20° C. and 100° C., preferably between 0° C. and 50° C.

The process (I) according to the invention is characterized in that compounds of the formulae (I-1-a) to (I-2-a) are in each case reacted with (Iα) compounds of the formula (XII), if appropriate in the presence of a diluent and if appropriate in the presence of a catalyst, or (Iβ) with compounds of the formula (XIII), if appropriate in the presence of a diluent and if appropriate in the presence of an acid binder.

In the preparation process (Iα), approximately 1 mol of isocyanate of the formula (XII) is reacted per mole of starting material of the formulae (I-1-a) to (I-2-a), at from 0 to 100° C., preferably at from 20 to 50° C.

The process (Iα) is preferably carried out in the presence of a diluent.

Suitable diluents are all inert organic solvents, such as aromatic hydrocarbons, halogenated hydrocarbons, ethers, amides, nitriles, sulphones or sulphoxides.

If appropriate, catalysts may be added to accelerate the reaction. Very advantageously, the catalysts which are employed are organotin compounds, such as, for example, dibutyltin dilaurate.

The reaction is preferably carried out at atmospheric pressure.

In the preparation process (Iβ), approximately 1 mol of carbamoyl chloride of the formula (XIII) is reacted per mole of starting material of the formulae (I-1-a) to (I-2-a), at from 0 to 150° C., preferably at from 20 to 70° C.

Suitable diluents which are added, if appropriate, are all inert polar organic solvents, such as ethers, carboxylic esters, nitrites, ketones, amides, sulphones, sulphoxides or halogenated hydrocarbons.

Preference is given to using dimethyl sulphoxide, tetrahydrofuran, dimethylformamide or methylene chloride.

If, in a preferred embodiment, the enolate salt of the compounds (I-1-a) to (I-2-a) is prepared by addition of strong deprotonating agents (such as, for example, sodium hydride or potassium tert-butoxide), it is not necessary to add further acid binders.

If acid binders are employed, these are customary inorganic or organic bases, for example sodium hydroxide, sodium carbonate, potassium carbonate triethylamine or pyridine.

The reaction can be carried out at atmospheric pressure or under elevated pressure and is preferably carried out at atmospheric pressure. Work-up is carried out by customary methods.

The active compounds are suitable for controlling animal pests, preferably arthropods and nematodes, in particular insects and arachnids, which are encountered in agriculture, in forestry, in the protection of stored products and of materials, and in the hygiene sector. They are active against normally sensitive and resistant species and against all or some stages of development. The abovementioned pests include: From the order of the Isopoda, for example, Oniscus asellus, Armadillidium vulgare and Porcellio scaber.

From the order of the *Diplopoda*, for example, *Blaniulus guttulatus*.

From the order of the *Chilopoda*, for example, *Geophilus carpophagus* and *Scutigera* spp.

From the order of the *Symphyla*, for example, *Scutigerella immaculata*.

From the order of the *Thysanura*, for example, *Lepisma saccharina*.

From the order of the *Collembola*, for example, *Onychiurus armatus*.

From the order of the *Orthoptera*, for example, *Acheta domesticus, Gryllotalpa* spp., *Locusta migratoria migratorioides, Melanoplus* spp. and *Schistocerca gregaria*.

From the order of the *Blattaria*, for example, *Blatta orientalis, Periplaneta americana, Leucophaea maderae* and *Blattella germanica*.

From the order of the *Dermaptera*, for example, Forficula auricularia.

From the order of the *Isoptera*, for example, *Reticulitermes* spp.

From the order of the Phthiraptera, for example, Pediculus humanus corporis, *Haematopinus* spp., *Linognathus* spp., *Trichodectes* spp. and *Damalinia* spp.

From the order of the *Thysanoptera*, for example, *Hercinothrips femoralis, Thrips tabaci, Thrips palmi* and *Frankliniella occidentalis.*

From the order of the *Heteroptera*, for example, *Eurygaster* spp., *Dysdercus intermedius, Piesma quadrata, Cimex lectularius, Rhodnius prolixus* and *Triatoma* spp.

From the order of the *Homoptera*, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix, Pemphigus* spp., *Macrosiphum avenae, Myzus* spp., Phorodon humuli, *Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp. and *Psylla* spp.

From the order of the *Lepidoptera*, for example, *Pectinophora gossypiella, Bupalus piniarius, Cheimatobia brumata, Lithocolletis blancardella, Hyponomeuta padella, Plutella xylostella, Malacosoma neustria, Euproctis chrysorrhoea, Lymantna* spp., *Bucculatrix thurberiella, Phyllocnistis citrella, Agrotis* spp., *Euxoa* spp., *Feltia* spp., *Earias insulana, Heliothis* spp., *Mamestra brassicae, Panolis flammea, Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana, Cnaphalocerus* spp. and *Oulema oryzae.*

From the order of the *Coleoptera*, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., Oryzaephilus *surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon soistitialis, Costelytra zealandica* and *Lissorhoptrus oryzophilus.*

From the order of the *Hymenoptera*, for example, *Diprion* spp., *Hoplocampa* spp., *Lasius* spp., *Monomorium pharaonis* and *Vespa* spp.

From the order of the *Diptera*, for example, *Aedes* spp., *Anopheles* spp., *Culex* spp., *Drosophila melanogaster, Musca* spp., *Fannia* spp., *Calliphora* erythrocephala, *Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., Pegomyia hyoscyami, *Ceratitis capitata, Dacus oleae, Tipula paludosa, Hylemyia* spp. and *Liriomyza* spp.

From the order of the *Siphonaptera*, for example, *Xenopsylla cheopis* and *Ceratophyllus* spp.

From the class of the *Arachnida*, for example, *Scorpio maurus, Latrodectus mactans, Acarus siro, Argas* spp., *Ornithodoros* spp., *Derrnanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* spp., *Hemitarsonemus* spp. and *Brevipalpus* spp.

The plant-parasitic nematodes include, for example, *Pratylenchus* spp., *Radopholus similis, Ditylenchus dipsaci, Tylenchulus semipenetrans, Heterodera* spp., *Globodera* spp., *Meloidogyne* spp., *Aphelenchoides* spp., *Longidorus* spp., *Xiphinema* spp., *Trichodorus* spp. and *Bursaphelenchus* spp.

The active compounds can be converted into the customary formulations, such as solutions, emulsions, wettable powders, suspensions, powders, dusts, pastes, soluble powders, granules, suspension-emulsion concentrates, natural and synthetic materials impregnated with active compound, and microencapsulations in polymeric substances.

These formulations are produced in a known manner, for example by mixing the active compounds with extenders, that is, liquid solvents, and/or solid carriers, optionally with the use of surfactants, that is emulsifiers and/or dispersants, and/or foam-formers.

If the extender used is water, it is also possible to employ for example organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethylformamide and dimethyl sulphoxide, and also water.

Suitable solid carriers are:
for example ammonium salts and ground natural minerals such as kaolins, clays, talc, chalk, quartz, attapulgite, montmorillonite or diatomaceous earth, and ground synthetic minerals, such as finely divided silica, alumina and silicates; suitable solid carriers for granules are: for example crushed and fractionated natural rocks such as calcite, marble, purnice, sepiolite and dolomite, and also synthetic granules of inorganic and organic meals, and granules of organic material such as sawdust, coconut shells, maize cobs and tobacco stalks; suitable emulsifiers and/or foam-formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are: for example lignosulphite waste liquors and methylcellulose.

Tackifiers such as carboxymethylcellulose and natural and synthetic polymers in the form of powders, granules or latexes, such as gum arabic, polyvinyl alcohol and polyvinyl acetate, as well as natural phospholipids such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95% by weight of active compound, preferably between 0.5 and 90%.

The active compound according to the invention can be present in its commercially available formulations and in the use forms, prepared from these formulations, as a mixture with other active compounds, such as insecticides, attractants, sterilizing agents, bactericides, acaricides, nematicides, fungicides, growth-regulating substances or herbicides. The insecticides include, for example, phosphoric acid esters, carbamates, carboxylates, chlorinated hydrocarbons, phenylureas and substances produced by microorganisms, inter alia.

Particularly favourable examples of co-components in mixtures are the following compounds:

Fungicides:
aldimorph, ampropylfos, ampropylfos potassium, andoprim, anilazine, azaconazole, azoxystrobin, benalaxyl, benodanil, benomyl, benzamacril, benzamacril-isobutyl, bialaphos, binapacryl, biphenyl, bitertanol, blasticidin-S, bromuconazole, bupirimate, buthiobate,
calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram,
debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon,
edifenphos, epoxiconazole, etaconazole, ethirimol, etridiazole,
famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminium, fosetyl-sodium, fthalide, fuberidazole, furalaxyl, furametpyr, furcarbonil, furconazole, furconazole-cis, furmecyclox,
guazatine,
hexachlorobenzene, hexaconazole, hymexazole,
imazalil, imibenconazole, iminoctadine, iminoctadine albesilate, iminoctadine triacetate, iodocarb, ipconazole, iprobenfos (]]BP), iprodione, irumamycin, isoprothiolane, isovaledione,
kasugamycin, kresoxim-methyl, copper preparations, such as: copper hydroxide, copper naphthenate, copper oxychloride, copper sulphate, copper oxide, oxine-copper and Bordeaux mixture,
mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin,
nickel dimethyldithiocarbamate, nitrothal-isopropyl, nuarimol,
ofurace, oxadixyl, oxamocarb, oxolinic acid, oxycarboxim, oxyfenthiin,
paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur,
quinconazole, quintozene (PCNB),
sulphur and sulphur preparations,
tebuconazole, tecloftalam, tecnazene, tetcyclacis, tetraconazole, thiabendazole, thicyofen, thifluzamide, thiophanate-methyl, thiram, tioxymid, toiclofos-methyl, tolylfluanid, triadimefon, triadimenol, triazbutil, triazoxide, trichlamide, tricyclazole, tridemorph, triflumizole, triforine, triticonazole,
uniconazole,
validamycin A, vinclozolin, viniconazole,
zarilamide, zineb, ziram and also
Dagger G,
OK-8705,
OK-8801,
α-(1,1-dimethylethyl)-β-(2-phenoxyethyl)-1H-1,2,4-triazole-1-ethanol,
α-(2,4-dichlorophenyl)-β-fluoro-β-propyl-1H-1,2,4-triazole-1-ethanol,
α-(2,4-dichlorophenyl)-β-methoxy-α-methyl-1H-1,2,4-triazole-1-ethanol,
α-(5-methyl-1,3-dioxan-5-yl)-β-[[4-(trifluoromethyl)-phenyl]-methylene]-1H-1,2,4-triazole-1-ethanol,
(5RS,6RS)-6-hydroxy-2,2,7,7-tetramethyl-5-(1H-1,2,4-triazol-1-yl)-3-octanone,
(E)-α-(methoxyimino)-N-methyl-2-phenoxy-phenylacetamide,
isopropyl {2-methyl-1-[[[1-(4-methylphenyl)-ethyl]-amino]-carbonyl]-propyl}-carbamate,
1-(2,4-dichlorophenyl)-2-(1H-1,2,4-triazol-1-yl)-ethanone-O-(phenylmethyl)-oxime,
1-(2-methyl-1-naphthalenyl)-1H-pyrrole-2,5-dione,
1-(3,5-dichlorophenyl)-3-(2-propenyl)-2,5-pyrrolidinedione,
1-[(diiodomethyl)-sulphonyl]-4-methyl-benzene,
1-[[2-(2,4-dichlorophenyl)-1,3-dioxolan-2-yl]-methyl]-1H-imidazole,
1-[[2-(4-chlorophenyl)-3-phenyloxiranyl]-methyl]-1H-1,2,4-triazole,
1-[1-[2-[(2,4-dichlorophenyl)-methoxy]-phenyl]-ethenyl]-1H-imidazole,
1-methyl-5-nonyl-2-(phenylmethyl)-3-pyrrolidinol,
2',6'-dibromo-2-methyl-4'-trifluoromethoxy4'-trifluoromethyl-1,3-thiazole-5-carboxanilide,
2,2-dichloro-N-[1-(4-chlorophenyl)-ethyl]-1-ethyl-3-methyl-cyclopropanecarboxamide,
2,6-dichloro-5-(methylthio)$_4$-pyrimidinyl-thiocyanate,
2,6-dichloro-N-(4-trifluoromethylbenzyl)-benzamide,
2,6-dichloro-N-[[4-(trifluoromethyl)-phenyl]-methyl]-benzamide,
2-(2,3,3-triiodo-2-propenyl)-2H-tetrazole,
2-[(1-methylethyl)sulphonyl]-5-(trichloromethyl)-1,3,4-thiadiazole,
2-[[6-deoxy-4-O-(4-O-methyl-α-D-glycopyranosyl)-α-D-glucopyranosyl]-amino]4-methoxy-1H-pyrrolo[2,3-d]pyrimidine-5-carbonitrile,
2-aminobutane,
2-bromo2-(bromomethyl)-pentanedinitrile,
2-chloro-N-(2,3-dihydro-1,1,3-trimethyl-1H-inden-4-yl)-3-pyridinecarboxamide,
2-chloro-N-(2,6-dimethylphenyl)-N-(isothiocyanato-methyl)-acetamide,
2-phenylphenol (OPP),
3,4-dichloro-1-[4-(difluoromethoxy)-phenyl]-1H-pyrrole-2,5-dione,
3,5-dichloro-N-[cyano-[(1-methyl-2-propynyl)-oxy]-methyl]-benzamide,
3-(1,1-dimethylpropyl)-1-oxo-1H-indene-2-carboni tri le,
3-[2-(4-chlorophenyl)-5-ethoxy-3-isoxazolidinyl]-pyri dine,
4-chloro-2-cyano-N,N-dimethyl-5-(4-methylphenyl)-1H-imidazole-1-sulphonamide,
4-methyl-tetrazolo[1,5-a]quinazolin-5(4H)-one,
8-(1,1-di methylethyl)-N-ethyl-N-propyl-1,4-dioxaspiro[4.5]decane-2-methanamine, 8-hydroxyquinoline sulphate,
9H-xanthene-2-[(phenylamino)-carbonyl]-9-carboxylic hydrazide,
bis-(1-methylethyl)-3-methyl 4-[(3-methylbenzoyl)-oxy]-2,5-thiophenedicarboxylate,
cis-1-(4-chlorophenyl)-2-(1H-1,2,4-triazol-1-yl)-cycloheptanol,
cis4-[3-[4-(1, 1-di methyl propyl)-phenyl-2-methylpropyl]-2,6-dimethy]-morpholinehydrochloride,
ethyl [(4-chlorophenyl)-azo]-cyanoacetate,
potassium hydrogen carbonate,
methanetetrathiol sodium salt,
methyl 1-(2,3-dihydro-2,2-dimethyl-1H-inden-1-yl)-1H-imidazole-5-carboxylate,
methyl N-(2,6-dimethylphenyl)-N-(5-isoxazolylcarbonyl)-DL-alaninate,
methyl N-(chloroacetyl)-N-(2,6-dimethylphenyl)-DL-alaninate,
N-(2,3-dichloro4-hydroxyphenyl)-1-methyl-cyclohexanecarboxamide,
N-(2,6-dimethylphenyl)-2-methoxy-N-(tetrahydr-2-oxo-3-furanyl)-acetamide,
N-(2,6-di methylphenyl)-2-methoxy-N-(tetrahydro-2-oxo-3-thienyl)-acetamide,
N-(2-chloro4-nitrophenyl)-4-methyl-3-nitro-benzenesulphonamide,
N-(4-cycl ohexylphenyl)-1,4,5,6-tetrahydro-2-pyri midinamine,
N-(4-hexylphenyl)-1,4,5,6-tetrahydro-2-pyri midinamine,
N-(5-chloro-2-methylphenyl)-2-methoxy-N-(2-oxo-3-oxazolidinyl)-acetamide,
N-(6-methoxy)-3-pyridinyl)-cyclopropanecarboxamide,
N-[2,2,2-trichloro-1-[(chloroacetyl)-amino]-ethyl]-benzamide,
N-[3-chloro4,5-bis(2-propinyloxy)-phenyl]-N'-methoxy-methanimidamide,
N-form yl-N-hydroxy-DL-alanine-sodium salt,
O,O-diethyl [2-(dipropylamino)-2-oxoethyl]-ethylphosphoramidothioate,
O-methyl S-phenyl phenylpropylphosphoramidothioate,
S-methyl 1,2,3-benzothiadiazole-7-carbothioate,
spiro[2H]-1-benzopyrane-2,1'(3'H)-isobenzofuran-3'-one.

Bactericides:
bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/acaricides nematicides:
abamectin, acephate, acetamiprid, acrinathrin, alanycarb, aldicarb, aldoxycarb, alphacypermethrin, alphamethrin, amitraz, avermectin, AZ 60541, azadirachtin, azamethiphos, azinphos A, azinphos M, azocyclotin,
*Bacillus popilliae, Bacillus sphaericus, Bacillus subtilis, Bacillus thuringiensis, Baculoviridae, Beauveria bassiana, Beauveria tenella,* bendiocarb, benfuracarb, bensultap, benzoximate, betacyfluthrin, bifenazate, bifenthrin, bioethanomethrin, biopermethrin, BPMC, bromophos A, bufencarb, buprofezin, butathiofos, butocarboxim, butylpyridaben,
cadusafos, carbaryl, carbofuran, carbophenothion, carbosulfan, cartap, chloethocarb, chlorethoxyfos, chlorfenapyr, chlorfenvinphos, chlorfluazuron, chlormephos, chlorpyrifos, chlorpyrifos M, chlovaporthrin, cis-resmethrin, cispermethrin, clocythrin, cloethocarb, clofentezine, cyanophos, cyprone, cycloprothrin, cyfluthrin, cyhalothrin, cyhexatin, cypermethrin, cyromazine, deltamethrin, demeton M, demeton S, demeton-S-methyl, diafenthiuron, diazinon, dichlorvos, diflubenzuron, dimethoate, dimethylvinphos, diofenolan, disulfoton, docusat-sodium, dofenapyn,
eflusilanate, emamectin, empenthrin, endosulfan, *Entomopfthora* spp., esfenvalerate, ethiofencarb, ethion, ethoprophos, etofenprox, etoxazole, etrimfos,
fenamiphos, fenazaquin, fenbutatin oxide, fenitrothion, fenothiocarb, fenoxacrim, fenoxycarb, fenpropathrin, fenpyrad, fenpyrithrin, fenpyroximate, fenvalerate, fipronil, fluazinam, fluazuron, flubrocythrinate, flucycloxuron, flucythrinate, flufenoxuron, flutenzine, fluvalinate, fonophos, fosmethilan, fosthiazate, fubfenprox, furathiocarb,
granulosis viruses,
halofenozide, HCH, heptenophos, hexaflumuron, hexythiazox, hydroprene,
imidacloprid, isazofos, isofenphos, isoxathion, ivermectin,
nuclear polyhedrosis viruses,
lambda-cyhalothrin, lufenuron,
malathion, mecarbam, metaldehyde, methamidophos, metharhizium anisopliae, metharhizium flavoviride, methidathion, methiocarb, methomyl, methoxyfenozide, metolcarb, metoxadiazone, mevinphos, milbemectin, monocrotophos,
naled, nitenpyram, nithiazine, novaluron,
omethoate, oxamyl, oxydemethon M,
*Paecilomyces fumosoroseus,* parathion A, parathion M, permethrin, phenthoate, phorate, phosalone, phosmet, phosphamidon, phoxim, pirimicarb, pirimiphos A, pirimiphos M, profenofos, promecarb, propoxur, prothiofos, prothoate, pymetrozine, pyraclofos, pyresmethrin, pyrethrum, pyridaben, pyridathion, pyrimidifen, pyriproxyfen,
quinalphos,
ribavirin,
salithion, sebufos, silafluofen, spinosad, sulfotep, sulprofos,
tau-fluvalinate, tebufenozide, tebufenpyrad, tebupirimiphos, teflubenzuron, tefluthrin, temephos, temivinphos, terbufos, tetrachlorvinphos, thetacypermethrin, thiamethoxam, thiapronil, thiatriphos, thiocyclam hydrogen oxalate, thiodicarb, thiofanox, thuringiensin, tralocythrin, tralomethrin, triarathene, triazamate, triazophos, triazurone, trichlophenidine, trichlorfon, triflumuron, trimethacarb,
vamidothion, vaniliprole, *Verticillium lecanii,*
YI 5302,
zeta-cypermethrin, zolaprofos,
(1R-cis)-[5-(phenylmethyl)-3-furanyl]-methyl 3-[(dihydro-2-oxo-3(2H)-furanylidene)-methyl]-2,2-di methylcyclopropanecarboxylate,
(3-phenoxyphenyl)-methyl 2,2,3,3-tetramethylcyclo-propanecarboxylate,
1-[(2-chloro-5-thiazolyl)methyl]tetrahydro-3,5-di methyl-N-nitro-11,3,5-triazi ne-2(1H)-imine,
2-(2-chloro6-fluorophenyl)-4-[4-(1,1-dimethylethyl) phenyl]4,5-dihydro-oxazole,
2-(acetyloxy)-3-dodecyl-1,4-naphthalenedione,
2-chloro-N-[[[4-(1-phenylethoxy)-phenyl]-amino]-carbonyl]-benzamide,
2-chloro-N-[[[4-(2,2-dichloro-1,1-difluoroethoxy)-phenyl]-amino]-carbonyl]-benzamide,
3-methylphenyl propylcarbamate,
4-[4-(4-ethoxyphenyl)₄-methylpentyl]-1-fluoro-2-phenoxy-benzene,
4-chloro-2-(1,1-dimethylethyl)-5-[[2-(2,6-di methyl-4-phenoxyphenoxy)ethyl]thio]-3(2H)-pyridazinone, 4-chloro-2-(2-chloro-2-methylpropyl)-5-[(6-iodo-3-pyridinyl)methoxy]-3(2H)-pyridazinone,
4-chloro-5-[(6-chloro-3-pyridinyl)methoxy]-2-(3,4-dichlorophenyl)-3 (2H)-pyridazinone,
Bacillus thuringiensis strain EG-2348,
2-benzoyl-1-(1,1-di methylethyl)-hydrazinobenzoic acid,
2,2-dimethyl-3-(2,4-dichlorophenyl)-2-oxo-1-oxaspiro[4.5]dec-3-en-4-yl butanoate,
[3-[(6-chloro-3-pyridinyl)methyl]-2-thiazolidinylidene]-cyanamide,
dihydro-2-(ni tromethylene)-2H- 1,3-thi azi ne-3 (4H)-carboxaldehyde,
ethyl [2-[[1,6-dihydro-6-oxo-1-(phenylmethyl)$_4$-pyridazinyl]oxy]ethyl]-carbamate,
N-(3,4,4-trifluoro-1-oxo-3-butenyl)glycine,
N-(4-chlorophenyl)-3-[4-(difluoromethoxy)phenyl]-4,5-dihydro4-phenyl-1H-pyrazole-1-carboxamide,
N-[(2-chloro-5-thiazolyl)methyl]-N'-methyl-N''-nitroguanidine,
N-methyl-N'-(N-methyl-2-propenyl)-1,2-hydrazinedicarbothioamide,
N-methyl-N'-2-propenyl-1,2-hydrazinedicarbothioamide,
O,O-diethyl [2-(dipropylamino)-2-oxoethyl]-ethylphosphoramidothioate.

A mixture with other known active compounds, such as herbicides, or with fertilizers and growth regulators is also possible.

The active compounds according to the invention can furthermore be present when used as insecticides in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms. When used against hygiene pests and pests of stored products, the active compound is distinguished by an excellent residual action on wood and clay as well as a good stability to alkali on limed substrates.

The active compounds according to the invention act not only against plant, hygiene and stored product pests, but also in the veterinary medicine sector against animal parasites (ectoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp. and *Solenopotes* spp.

From the order of the Mallophagida and the suborders Amblycerina and ischnocerina, for example, *Trimenopon* spp., *Menopon* spp., *Trinoton* spp., *Bovicola* spp., *Wemeckiella* spp., *Lepikentron* spp., *Damalina* spp., *Trichodectes* spp. and *Felicola* spp.

From the order *Diptera* and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oesirus* spp., *Hypoderma* spp., *Gasterophilus* spp., *Hippobosca* spp., *Lipoptena* spp. and *Melophagus* spp.

From the order of the Siphonapterida, for example, *Pulex* spp., *Ctenocephalides* spp., *Xenopsylla* spp. and *Ceratophyllus* spp.

From the order of the Heteropterida, for example, *Cimex* spp., *Triatoma* spp., *Rhodnius* spp. and Panstrongylus spp.

From the order of the Blattarida, for example, *Blatta orientalis, Periplaneta* americans, Blattela germanica and Supella spp.

From the subclass of the Acaria (Acarida) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., Dermanyssus spp., *Raillietia* spp., *Pneumonyssus* spp., *Sternostoma* spp and *Varroa* spp.

From the order of the Actinedida (Prostigmata) and Acaridida (Astigmata), for 1 example, *Acarapis* spp., *Cheyletiella* spp., *Orithocheyletia* spp., *Myobia* spp., *Psorergates* spp., *Demodex* spp., *Trombicula* spp., Listrophorus spp., *Acarus* spp., *Tyrophagus* spp., *Caloglyphus* spp., *Hypodectes* spp, *Pterolichus* spp., *Psoroptes* spp., *Chorioptes* spp., *Otodectes* spp., Sarcoptes spp., *Notoedres* spp., *Knemidocoptes* spp., *Cytodites* spp. and *Laminosioptes* spp.

They are highly effective against *Boophilus microplus* and *Lucilia* cuprina for example.

The active compounds of the formula (I) according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so called test animals, such as, for example, hamsters, guinea pigs, rats and mice. By controlling these arthropods, cases of death and reduction in productivity (for meat, milk, wool, hides, eggs, honey etc.) should be diminished, so that more economic and easier animal husbandry is possible by use of the active compounds according to the invention.

The active compounds according to the invention are used in the veterinary sector in a known manner by enteral administration in the form of, for example, tablets, capsules, potions, drenches, granules, pastes, boluses, the feed-through process and suppositories, by parenteral administration, such as, for example, by injections (intramuscular, subcutaneous, intravenous, intraperitoneal and the like), implants, by nasal administration, by dermal use in the form, for example, of dipping or bathing, spraying, pouring on and spotting on, washing and powdering, and also with the aid of moulded articles containing the active compound, such as collars, ear marks, tail marks, limb bands, halters, marking devices and the like.

When used for cattle, poultry, pets and the like, the active compounds of the formula (I) can be used as formulations (for example powders, emulsions, free-flowing compositions), which comprise the active compounds in an amount of 1 to 80% by weight, directly or after 100 to 10 000-fold dilution, or they can be used as a chemical bath.

It has furthermore been found that the compounds according to the invention also have a strong insecticidal action against insects which destroy industrial materials.

The following insects may be mentioned as examples and as being preferred—but without any limitati on:

Beetles, such as

*Hylotrupes bajulus, Chlorophorus pilosis, Anobium punctatum, Xestobium rufovillosum, Ptilinus pecticomris, Dendrobium pertinex, Enmobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec. *Tryptodendron* spec. *Apate monachus, Bostrychus capucins, Heterobostrychus brunneus* and *Sinoxylon* spec. *Dinoderus minutus.*

Hymenopterons, such as

Sirex juvencus, Urocerus gigas, Urocerus gigas taignus and Urocerus augur.

Termites, such as

Kalotermes flavicollis, *Cryptotermes* brevis, Heterotermes indicola, *Reticulitermes flavipes, Reticulitermes santonensis, Reticulitermes* lucifugus, *Mastotermes* darwiniensis, *Zootermopsis* nevadensis and *Coptotermes formosanus.*

Bristletails, such as Lepisma saccarina.

Industrial materials in the present connection are to be understood as meaning nonliving materials, such as, preferably, plastics, adhesives, sizes, papers and cards, leather, wood and processed wood products and coating compositions.

Wood and processed wood products are materials to be protected, especially preferably, from insect infestation.

Wood and processed wood products which can be protected by the agent according to the invention or mixtures comprising it are to be understood as meaning, for example: building timber, wooden beams, railway sleepers, bridge components, boat jetties, wooden vehicles, boxes, pallets, containers, telegraph poles, wood paneling, wooden windows and doors, plywood, chipboard, joinery or wooden products which are used quite generally in house-building or in building joinery.

The active compounds can be used as such, in the form of concentrates or in generally customary formulations, such as powders, granules, solutions, suspensions, emulsions or pastes.

The formulations mentioned can be prepared in a manner known per se, for example by mixing the active compounds with at least one solvent or diluent, emulsifier, dispersing agent and/or binder or fixing agent, a water repellent, if appropriate siccatives and UV stabilizers and if appropriate dyestuffs and pigments, and also other processing auxiliaries.

The insecticidal compositions or concentrates used for the preservation of wood and wood-derived timber products comprise the active compound according to the invention in a concentration of 0.0001 to 95% by weight, in particular 0.001 to 60% by weight.

The amount of the compositions or concentrates employed depends on the nature and occurrence of the insects and on the medium. The optimum amount employed can be determined for the use in each case by a series of tests. In general, however, it is sufficient to employ 0.0001 to 20% by weight, preferably 0.001 to 10% by weight, of the active compound, based on the material to be preserved.

Solvents and/or diluents which are used are an organic chemical solvent or solvent mixture and/or an oily or oil-like organic chemical solvent or solvent mixture of low volatility and/or a polar organic chemical solvent or solvent mixture and/or water, and if appropriate an emulsifier and/or wetting agent.

Organic chemical solvents which are preferably used are oily or oil-like solvents having an evaporation number above 35 and a flashpoint above 30° C., preferably above 45° C. Substances which are used as such oily or oil-like water-insoluble solvents of low volatility are appropriate mineral oils or aromatic fractions thereof, or solvent mixtures containing mineral oils, preferably white spirit, petroleum and/or alkylbenzene.

Mineral oils having a boiling range from 170 to 220° C., white spirit having a boiling range from 170 to 220° C., spindle oil having a boiling range from 250 to 350° C., petroleum and aromatics having a boiling range from 160 to 280° C., turpentine oil and the like, are advantageously employed.

In a preferred embodiment, liquid aliphatic hydrocarbons having a boiling range from 180 to 210° C. or high-boiling mixtures of aromatic and aliphatic hydrocarbons having a boiling range from 180 to 220° C. and/or spindle oil and/or monochloronaphthalene, preferably a-monochloro-naphthalene, are used.

The organic oily or oil-like solvents of low volatility which have an evaporation number above 35 and a flashpoint above 30° C., preferably above 45° C., can be replaced in part by organic chemical solvents of high or medium volatility, providing that the solvent mixture likewise has an evaporation number above 35 and a flashpoint above 30° C., preferably above 45° C., and that the insecticide/fungicide mixture is soluble or emulsifiable in this solvent mixture.

According to a preferred embodiment, some of the organic chemical solvent or solvent mixture is replaced by an aliphatic polar organic chemical solvent or solvent mixture. Aliphatic organic chemical solvents containing hydroxyl and/or ester and/or ether groups, such as, for example, glycol ethers, esters or the like, are preferably used.

Organic chemical binders which are used in the context of the present invention are the synthetic resins and/or binding drying oils which are known per se, are water-dilutable and/or are soluble or dispersible or emulsifiable in the organic chemical solvents employed, in particular binders consisting of or comprising an acrylate resin, a vinyl resin, for example polyvinyl acetate, polyester resin, polycondensation or polyaddition resin, polyurethane resin, alkyd resin or modified alkyd resin, phenolic resin, hydrocarbon resin, such as indene-cumarone resin, silicone resin, drying vegetable oils and/or drying oils and/or physically drying binders based on a natural and/or synthetic resin.

The synthetic resin used as the binder can be employed in the form of an emulsion, dispersion or solution. Bitumen or bituminous substances can also be used as binders in an amount of up to 10% by weight. Dyestuffs, pigments, water-repelling agents, odour correctants and inhibitors or anticorrosive agents and the like which are known per se can additionally be employed.

It is preferred according to the invention for the composition or concentrate to comprise, as the organic chemical binder, at least one alkyd resin or modified alkyd resin and/or one drying vegetable oil. Alkyd resins having an oil content of more than 45% by weight, preferably 50 to 68% by weight, are preferably used according to the invention.

All or some of the binder mentioned can be replaced by a fixing agent (mixture) or a plasticizer (mixture). These additives are intended to prevent evaporation of the active compounds and crystallization or precipitation. They preferably replace 0.01 to 30% of the binder (based on 100% of the binder employed).

The plasticizers originate from the chemical classes of phthalic acid esters, such as dibutyl, dioctyl or benzyl butyl phthalate, phosphoric acid esters, such as tributyl phosphate, adipic acid esters, such as di-(2-ethylhexyl) adipate, stearates, such as butyl stearate or amyl stearate, oleates, such as butyl oleate, glycerol ethers or higher molecular weight glycol ethers, glycerol esters and p-toluenesulphonic acid esters.

Fixing agents are based chemically on polyvinyl alkyl ethers, such as, for example, polyvinyl methyl ether or ketones, such as benzophenone or ethylenebenzophenone.

Possible solvents or diluents are, in particular, also water, if appropriate as a mixture with one or more of the abovementioned organic chemical solvents or diluents, emulsifiers and dispersing agents.

Particularly effective preservation of wood is achieved by impregnation processes on a large industrial scale, for example vacuum, double vacuum or pressure processes.

The ready-to-use compositions can also comprise other insecticides, if appropriate, and also one or more fungicides, if appropriate.

Possible additional mixing partners are, preferably, the insecticides and fungicides mentioned in WO 94/29 268. The compounds mentioned in this document are an explicit constituent of the present application.

Especially preferred mixing partners which may be mentioned are insecticides, such as chlorpyriphos, phoxim, silafluofin, alphamethrin, cyfluthrin, cypermethrin, deltamethrin, permethrin, imidacloprid, NI-25, flufenoxuron, hexaflumuron, transfluthrin, thiacloprid, methoxyphenoxide and triflumuron, and also fungicides, such as epoxyconazole, hexaconazole, azaconazole, propiconazole, tebuconazole, cyproconazole, metconazole, imazalil, dichlorfluanid, tolylfluanid, 3-iodo-2-propinyl-butyl carbamate, N-octyl-isothiazolin-3-one and 4,5-dichloro-N-octylisothiazolin-3-one.

The compounds according to the invention can at the same time be employed for protecting objects which come into contact with saltwater or brackish water, such as hulls, screens, nets, buildings, moorings and signalling systems, against fouling.

Fouling by sessile Oligochaeta, such as Serpulidae, and by shells and species from the Ledamorpha group (goose barnacles), such as various Lepas and Scalpellum species, or by species from the Balanomorpha group (acorn barnacles), such as Balanus or Pollicipes species, increases the frictional drag of ships and, as a consequence, leads to a marked increase in operation costs owing to higher energy consumption and additionally frequent residence in the dry dock.

Apart from fouling by algae, for example *Ectocarpus* sp. and *Ceramium* sp., fouling by sessile Entomostraka groups, which come under the generic term Cirripedia (cirriped crustaceans), is of particular importance.

Surprisingly, it has now been found that the compounds according to the invention, alone or in combination with other active compounds, have an outstanding antifouling action.

Using the compounds according to the invention, alone or in combination with other active compounds, allows the use of heavy metals such as, for example, in bis-(trialkyltin) sulphides, tri-n-butyltin laurate, tri-n-butyltin chloride, copper(I) oxide, triethyltin chloride, tri-n-butyl(2-phenyl-4-chlorophenoxy)tin, tributyltin oxide, molybdenum disulphide, antimony oxide, polymeric butyl titanate, phenyl-(bispyridine)-bismuth chloride, tri-n-butyltin fluoride, manganese ethylenebisthiocarbamate, zinc dimethyldithiocarbamate, zinc ethylenebisthiocarbamate, zinc salts and copper salts of 2-pyridinethiol 1-oxide, bis-dimethyldithiocarbamoylzinc ethylene-bisthiocarbamate, zinc oxide, copper(I) ethylene-bisdithiocarbamate, copper thiocyanate, copper naphthenate and tributyltin halides to be dispensed with, or the concentration of these compounds substantially reduced.

If appropriate, the ready-to-use antifouling paints can additionally comprise other active compounds, preferably algicides, fungicides, herbicides, molluscicides, or other antifouling active compounds.

Preferably suitable components in combinations with the antifouling compositions according to the invention are:
algicides such as
2-tert-butylamino-4-cyclopropylamino-6-methylthio-1,3,5-triazine, dichlorophen, diuron, endothal, fentin acetate, isoproturon, methabenzthiazuron, oxyfluorfen, quinoclamine and terbutryn;
fungicides such as
benzo[b]thiophenecarboxylic acid cyclohexylamide S,S-dioxide, dichlofluanid, fluorfolpet, 3-iodo-2-propinyl butylcarbamate, tolylfluanid and azoles such as azaconazole, cyproconazole, epoxyconazole, hexaconazole, metconazole, propiconazole and tebuconazole;
molluscicides such as
fentin acetate, metaldehyde, methiocarb, niclosamid, thiodicarb and trimethacarb;
or conventional antifouling active compounds such as 4,5-dichloro-2-octyl-4-isothiazolin-3-one, diiodomethylparatryl sulphone, 2-(N,N-dimethylthiocarbamoylthio)-5-nitrothiazyl, potassium, copper, sodium and zinc salts of 2-pyridinethiol 1-oxide, pyridine-triphenylborane, tetrabutyldistannoxane, 2,3,5,6-tetrachloro4-(methylsulphonyl)-pyridine, 2,4,5,6-tetrachloroisophthalonitrile, tetramethylthiuram disulphide and 2,4,6-trichlorophenylmaleiimide.

The antifouling compositions used comprise the active compound according to the invention of the compounds according to the invention in a concentration of 0.001 to 50% by weight, in particular 0.01 to 20% by weight.

Moreover, the antifouling compositions according to the invention comprise the customary components such as, for example, those described in Ungerer, Chem. Ind. 1985, 37, 730–732 and Williams, Antifouling Marine Coatings, Noyes, Park Ridge, 1973.

Besides the algicidal, fungicidal, molluscicidal active compounds and insecticidal active compounds according to the invention, antifouling paints comprise, in particular, binders.

Examples of recognized binders are polyvinyl chloride in a solvent system, chlorinated rubber in a solvent system, acrylic resins in a solvent system, in particular in an aqueous system, vinyl chloride/vinyl acetate copolymer systems in the form of aqueous dispersions or in the form of organic solvent systems, butadiene/styrene/acrylonitrile rubbers, drying oils such as linseed oil, resin esters or modified hardened resins in combination with tar or bitumens, asphalt and epoxy compounds, small amounts of chlorine rubber, chlorinated polypropylene and vinyl resins.

If appropriate, paints also comprise inorganic pigments, organic pigments or colorants which are preferably insoluble in salt water. Paints may furthermore comprise materials such as colophonium to allow controlled release of the active compounds. Furthermore, the paints may comprise plasticizers, modifiers which affect the rheological properties and other conventional constituents. The compounds according to the invention or the abovementioned mixtures may also be incorporated into self-polishing antifouling systems.

The active compounds are also suitable for controlling animal pests, in particular insects, arachnids and mites, which are found in enclosed spaces such as, for example, dwellings, factory halls, offices, vehicle cabins and the like. They can be employed in domestic insecticide products for controlling these pests alone or in combination with other active compounds and auxiliaries. They are active against sensitive and resistant species and against all developmental stages. These pests include:

From the order of the Scorpionidea, for example, Buthus occilanus.

From the order of the Acarina, for example, Argas persicus, Argas reflexus, *Bryobia* ssp., Dermanyssus gallinae, Glyciphagus domesticus, Ornithodorus moubat, Rhipicephalus sanguineus, Trombicula alfreddugesi, Neutrombicula autumnalis, *Dermatophagoides* pteronissimus and Derrnatophagoides forinae.

From the order of the Araneae, for example, Aviculariidae and Araneidae.

From the order of the Opiliones, for example, Pseudoscorpiones chelifer, Pseudoscorpiones cheiridium and Opiliones phalangium.

From the order of the Isopoda, for example, Oniscus asellus and Porcellio scaber.

From the order of the Diplopoda, for example, Blaniulus guttulatus and *Polydesmus* spp.

From the order of the Chilopoda, for example, *Geophilus* spp.

From the order of the Zygentoma, for example, *Ctenolepisma* spp., Lepisma saccharina and Lepismodes inquilinus.

From the order of the Blattaria, for example, *Blatta* orientalies, *Blattella germanica, Blattella* asahinai, Leucophaea maderae, *Panchlora* spp., *Parcoblatta* spp., *Periplaneta* australasiae, *Periplaneta americana, Periplaneta* brunnea, *Periplaneta fuliginosa* and Supella longipalpa.

From the order of the Saltatoria, for example, Acheta domesticus.

From the order of the *Dermaptera*, for example, Forficula auricularia.

From the order of the *Isoptera*, for example, *Kalotermes* spp. and *Reticulitermes* spp.

From the order of the Psocoptera, for example, *Lepinatus* spp. and *Liposcelis* spp.

From the order of the Coleptera, for example, *Anthrenus* spp., *Attagenus* spp., *Dermestes* spp., Latheticus oryzae, *Necrobia* spp., *Ptinus* spp., Rhizopertha dominica, *Sitophilus* granarius, *Sitophilus oryzae, Sitophilus zeamais* and Stegobium paniceum.

From the order of the *Diptera*, for example, *Aedes aegypti, Aedes albopictus, Aedes* taeniorhynchus, *Anopheles* spp., *Calliphora* erythrocephala, Chrysozona pluvialis, *Culex* quinquefasciatus, *Culex* pipiens, *Culex* tarsalis, *Drosophila* spp., Fannia canicularis, *Musca domestica, Phlebotomus* spp., *Sarcophaga* carnaria, *Simulium* spp., *Stomoxys* calcitrans and Tipula paludosa.

From the order of the *Lepidoptera*, for example, *Achroia* grisella, *Galleria mellonella, Plodia* interpunctella, Tinea cloacella, Tinea pellionella and *Tineola* bisselliella.

From the order of the *Siphonaptera*, for example, *Ctenocephalides* canis, *Ctenocephalides felis, Pulex* irritans, *Tunga* penetrans and *Xenopsylla* cheopis.

From the order of the *Hymenoptera*, for example, Camponotus herculeanus, Lasius fuliginosus, Lasius niger, Lasius umbratus, *Monomorium pharaonis, Paravespula* spp. and Tetramorium caespitum.

From the order of the *Anoplura*, for example, Pediculus humanus capitis, Pediculus humanus corporis and Phthirus pubis.

From the order of the Heteroptera, for example, Cimex hemipterus, Cimex lectularius, Rhodinus prolixus and Triatoma infestans.

They are used in the household insecticides sector alone or in combination with other suitable active compounds such as phosphoric esters, carbamates, pyrethroids, growth regulators or active compounds from other known classes of insecticides.

They are used in aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propellerdriven evaporators, energy-free, or passive, evaporation systems, moth papers, moth bags and moth gels, as granules or dusts, in baits for spreading or in bait stations.

At certain concentrations or application rates, the compounds according to the invention may, if appropriate, also be used as herbicides and microbicides, for example as fungicides, antimycotics and bactericides. If appropriate, they may also be used as intermediates or precursors for the synthesis of further active compounds.

The active compounds according to the invention can be used as defoliants, desiccants, haulm killers and, especially, as weed killers. Weeds in the broadest sense are understood to mean all plants which grow in locations where they are undesired. Whether the substances according to the invention act as total or selective herbicides depends essentially on the amount used.

The active compounds according to the invention can be used, for example, in connection with the following plants:

Dicotyledonous weeds of the Genera: Sinapis, *Lepidium*, Galium, *Stellaria*, Matricaria, Anthemis, Galinsoga, *Chenopodium, Urtica*, Senecio, *Amaranthus*, Portulaca, *Xanthium*, Convolvulus, *Ipomoea, Polygonum*, Sesbania, *Ambrosia*, Cirsium, Carduus, Sonchus, *Solanum*, Rorippa, *Rotala, Lindernia*, Lamium, Veronica, *Abutilon*, Emex, *Datura*, Viola, Galeopsis, Papaver, Centaurea, *Trifolium*, Ranunculus and Taraxacum.

Dicotyledonous crops of the genera: *Gossypium*, Glycine, Beta, *Daucus, Phaseolus, Pisum, Solanum, Linum, Ipomoea, Vicia, Nicotiana, Lycopersicon, Arachis, Brassica, Lactuca, Cucumis*, and *Cucurbita.*

Monocotyledonous weeds of the Genera: Echinochloa, *Setaria, Panicum, Digitaria, Phleum, Poa, Festuca, Eleusine*, Brachiaria, *Lolium, Bromus, Avena, Cyperus, Sorghum, Agropyron*, Cynodon, *Monochoria*, Fimbristylis, *Sagittaria, Eleocharis, Scirpus*, Paspalurn, Ischaemum, Sphenoclea, Dactyloctenium, *Agrostis, Alopecurus*, Apera, Aegilops and *Phalaris.*

Monocotyledonous crops of the genera: *Oryza, Zea, Triticum, Hordeum, Avena, Secale, Sorghum, Panicum*, Saccharum, *Ananas*, Asparagus and *Allium.*

However, the use of the active compounds according to the invention is in no way restricted to these genera, but also extends in the same manner to other plants.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and recombinant methods or by combinations of these methods, including the transgenic plants and including the plant cultivars protectable or not protectable by plant breeders' rights. Plant parts are to be understood to mean all above-ground and underground parts and organs of plants, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offsets and seeds.

The treatment according to the invention of the plants and plant parts with the active compounds is carried out directly or by allowing the compounds to act on their surroundings, environment or storage space by the customary treatment methods, for example by immersion, spraying, evaporation, fogging, scattering, painting on and, in the case of propagation material, in particular in the case of seed, also by applying one or more coats.

The active compounds according to the invention are suitable, depending on the concentration, for the total control of weeds, for example on industrial terrain and rail tracks, and on paths and areas with and without tree plantings. Similarly, the active compounds according to the invention can be employed for controlling weeds in perennial crops, for example forests, decorative tree plantings, orchards, vineyards, citrus groves, nut orchards, banana plantations, coffee plantations, tea plantations, rubber plantations, oil palm plantations, cocoa plantations, soft fruit plantings and hop fields, on lawns, turf and pastureland, and for the selective control of weeds in annual crops.

The compounds of the formula (I) according to the invention have strong herbicidal activity and a broad activity spectrum when used on the soil or on above-ground parts of plants. To a certain extent, they are also suitable for the selective control of monocotyledonous and dicotyledonous weeds in monocotyledonous and dicotyledonous crops, both by the pre-emergence and by the post-emergence method.

The active compounds can be converted into the customary formulations, such as solutions, emulsions, wettable powders, suspensions, powders, dusts, pastes, soluble powders, granules, suspo-emulsion concentrates, natural and synthetic substances impregnated with active compound, and microencapsulations in polymeric substances.

These formulations are produced in a known manner, for example by mixing the active compounds with extenders, that is to say liquid solvents and/or solid carriers, optionally with the use of surfactants, that is to say emulsifiers and/or dispersants and/or foam formers.

If the extender used is water, it is also possible to use, for example, organic solvents as auxiliary solvents. Liquid solvents which are mainly suitable are: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol, and also their ethers and esters, ketones, such as acetone, methyl ethyl ketone, methyl isobutyl ketone or cyclohexanone, strongly polar solvents, such as dimethylformamide and dimethyl sulphoxide, and water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are: for example crushed and fractionated natural rocks, such as calcite, marble, pumice, sepiolite, dolomite and synthetic granules of inorganic and organic meals, and granules of organic material, such as sawdust, coconut shells, maize cobs and tobacco stalks; suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignosulphite waste liquors and methylcellulose.

Tackifiers, such as carboxymethylcellulose, natural and synthetic polymers in the form of powders, granules or latices, such as gum arabic, polyvinyl alcohol and polyvinyl acetate, and also natural phospholipids, such as cephalins and lecithins, and synthetic phospholipids can be used in the formulations. Other possible additives are mineral and vegetable oils.

It is possible to use colorants, such as inorganic pigments, for example iron oxide, titanium oxide, Prussian blue, and organic dyestuffs, such as alizarin dyestuffs, azo dyestuffs and metal phthalocyanine dyestuffs, and trace nutrients, such as salts of iron, manganese, boron, copper, cobalt, molybdenum and zinc.

The formulations generally comprise between 0.1 and 95 percent by weight of active compound, preferably between 0.5 and 90%.

For controlling weeds, the active compounds according to the invention, as such or in their formulations, can also be used as mixtures with known herbicides, finished formulations or tank mixes being possible.

Possible components for the mixtures are known herbicides, for example acetochlor, acifluorfen (-sodium), aclonifen, alachlor, alloxydim (-sodium), ametryne, amidochlor, amidosulfuron, anilofos, asulam, atrazine, azafenidin, azimsulfuron, benazolin (-ethyl), benfuresate, bensulfuron (-methyl), bentazone, benzofenap, benzoylprop (-ethyl), bialaphos, bifenox, bispyribac (-sodium), bromobutide, bromofenoxim, bromoxynil, butachlor, butroxydim, butylate, cafenstrole, caloxydim, carbetamide, carfentrazone (-ethyl), chlomethoxyfen, chloramben, chloridazon, chlorimuron (-ethyl), chlornitrofen, chlorsulfuron, chlortoluron, cinidon (-ethyl), cinmethylin, cinosulfuron, clethodim, clodinafop (-propargyl), clomazone, clomeprop, clopyralid, clopyrasulfuron (-methyl), cloransulam (-methyl), cumyluron, cyanazine, cybutryne, cycloate, cyclosulfamuron, cycloxydim, cyhalofop (-butyl), 2,4-D, 2,4-DB, 2,4-DP, desmedipham, diallate, dicamba, diclofop (-methyl), diclosulam, diethatyl (-ethyl), difenzoquat, diflufenican, diflufenzopyr, dimefuron, dimepiperate, dimethachlor, dimethametryn, dimethenamid, dimexyflam, dinitramine, diphenamid, diquat, dithiopyr, diuron, dymron, epropodan, EPTC, esprocarb, ethalfluralin, ethametsulfuron (-methyl), ethofumesate, ethoxyfen, ethoxysulfuron, etobenzanid, fenoxaprop (-P-ethyl), flamprop (-isopropyl), flamprop (-isopropyl-L), (flamprop-(methyl), flazasulfuron, fluazifop (-P-butyl), fluazolate, flucarbazone, flufenacet, flumetsulam, flumiclorac (-pentyl), flumioxazin, flumipropyn, flumetsulam, fluometuron, fluorochloridone, fluoroglycofen (-ethyl), flupoxam, flupropacil, flurpyrsulfuron (-methyl, -sodium), flurenol (-butyl), fluridone, fluroxypyr (-meptyl), flurprimidol, flurtamone, fluthiacet (-methyl), fluthiamide, fomesafen, glufosinate (-ammonium), glyphosate (-isopropylammonium), halosafen, haloxyfop (ethoxyethyl), haloxyfop (—P-methyl), hexazinone, imazamethabenz (-methyl), imazamethapyr, imazamox, imazapic, imazapyr, imazaquin, imazethapyr, imazosulfuron, iodosulfuron, ioxynil, isopropalin, isoproturon, isouron, isoxaben, isoxachlortole, isoxaflutole, isoxapyrifop, lactofen, lenacil, linuron, MCPA, MCPP, mefenacet, mesotrione, metamitron, metazachlor, methabenzthiazuron, metobenzuron, metobromuron, (alpha-) metolachlor, metosulam, metoxuron, metribuzin, metsulfuron (-methyl), molinate, monolinuron, naproanilide, napropamide, neburon, nicosulfuron, norflurazon, orbencarb, oryzalin, oxadiargyl, oxadiazon, oxasulfuron, oxaziclomefone, oxyfluorfen, paraquat, pelargonic acid, pendimethalin, pentoxazone, phenmedipham, piperophos, pretilachlor, primisulfuron (-methyl), prometryn, propachlor, propanil, propaquizafop, propisochlor, propyzamide, prosulfocarb, prosulfuron, pyraflufen (-ethyl), pyrazolate, pyrazosulfuron (-ethyl), pyrazoxyfen, pyribenzoxim, pyributicarb, pyridate, pyriminobac (-methyl), pyrithiobac (-sodium), quinchlorac, quinmerac, quinoclamine, quizalofop (-p-ethyl), quizalofop (-p-tefuryl), rimsulfuron, sethoxydim, simazine, simetryn, sulcotrione, sulfentrazone, sulfometuron (-methyl), sulfosate, sulfosulfuron, tebutam, tebuthiuron, tepraloxydim, terbuthylazine, terbutryn, thenylchlor, thiafluamide, thiazopyr, thidiazimin, thifensulfuron (-methyl), thiobencarb, tiocarbazil, tralkoxydim, triallate, triasulfuron, tribenuron (-methyl), triclopyr, tridiphane, trifluralin and and tritosulfuron.

A mixture with other known active compounds, such as fungicides, insecticides, acaricides, nematicides, bird repellents, plant nutrients and agents which improve soil structure, is also possible.

The active compounds can be used as such, in the form of the formulations or in the use forms prepared therefrom by further dilution, such as ready-to-use solutions, suspensions, emulsions, powders, pastes and granules. They are used in a customary manner, for example by watering, spraying, atomizing, or broadcasting.

The active compounds according to the invention can be applied both before and after emergence of the plants. They can also be incorporated into the soil before sowing.

The amount of active compound used can vary within a relatively wide range. It depends essentially on the nature of the desired effect. In general, the amounts used are between 1 g and 10 kg of active compound per hectare of soil surface, preferably between 5 g and 5 kg per ha.

The preparation and use of the active compounds according to the invention is illustrated by the examples below.

PREPARATION EXAMPLES

Example (I-1-a-1)

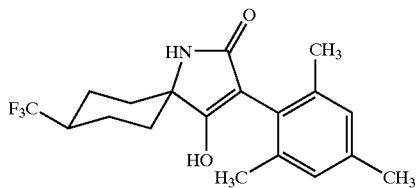

At 60° C., 9 g of the compound of Example (I-1) in 20 ml of anhydrous dimethylformamide (DMF) are added dropwise to 7.4 g of potassium tert-butoxide in 30 ml of DMF, and the mixture is stirred at 60° C. for 2 h. The reaction solution is then poured into 250 ml of ice-water and, at 0–10° C., acidified with concentrated hydrochloric acid to pH 2, and the solid is filtered off with suction and dried.

The crude product is boiled in methyl tert-butyl ether (MTBE)/n-hexane, filtered off with suction and dried.

Yield: 6.15 g (74% of theory); m.p.: >250° C.

The following compounds of the formula (I-1-a) were prepared similarly to Example (I-1-a-1) and in accordance with the general preparation instructions:

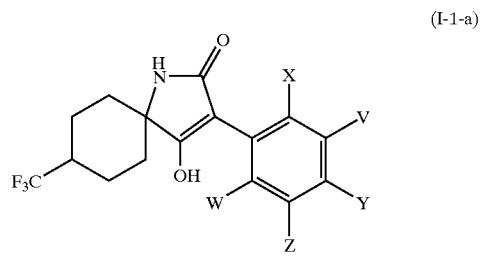

(I-1-a)

| Ex. No. | V | W | X | Y | Z | m.p. ° C. | Isomer |
|---|---|---|---|---|---|---|---|
| I-1-a-2 | H | H | CH$_3$ | H | CH$_3$ | 245 | β |
| I-1-a-3 | H | H | CH$_3$ | CH$_3$ | CH$_3$ | 175 | β |
| I-1-a-4 | H | Cl | Cl | CH$_3$ | H | >250 | β |
| I-1-a-5 | CH$_3$ | CH$_3$ | CH$_3$ | CH$_3$ | H | >250 | β |
| I-1-a-6 | H | CH$_3$ | CH$_3$ | Cl | H | >248 | β |
| I-1-a-7 | H | H | Br | H | CH$_3$ | 212 | β |

Example (I-1-b-1)

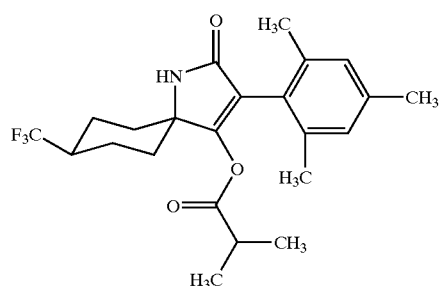

1.42 g of the compound of Example (I-1-a-1) are initially charged in 40 ml of anhydrous ethyl acetate and admixed with 0.62 ml (4.4 mmol) of triethylamine, and, at reflux, 0.46 ml (0.0046 mol) of isobutyryl chloride in 5 ml of anhydrous ethyl acetate is added dropwise. After 16 h at reflux, the mixture is concentrated and the residue is taken up in methylene chloride, washed 2× with 30 ml of 0.5 N NaOH, dried and concentrated. The residue is chromatographed on silica gel using methylene chloride/ethyl acetate 3:1.

Yield: 1.12 g (66% of theory); m.p.: >240° C.

The following compounds of the formula (I-1-b) were prepared similarly to Example (I-1-b-1) and in accordance with the general preparation instructions:

(I-1-b)

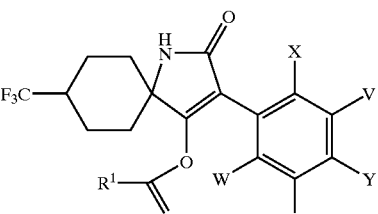

| Ex. No. | V | W | X | Y | Z | R¹ | m.p. ° C. | Isomer |
|---|---|---|---|---|---|---|---|---|
| I-1-b-2 | H | H | CH₃ | H | CH₃ | i-C₃H₇ | >240 | β |
| I-1-b-3 | H | H | CH₃ | CH₃ | CH₃ | i-C₃H₇ | 209 | β |
| I-1-b-4 | CH₃ | CH₃ | CH₃ | CH₃ | H | i-C₃H₇ | 236 | β |

Example (I-1-c-1)

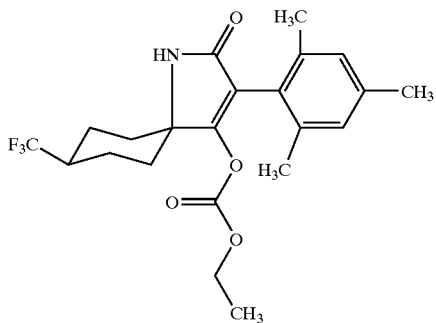

1.42 g of the compound of Example (I-1-a-1) are initially charged in 40 ml of anhydrous methylene chloride and admixed with 0.56 ml (4 mmol) of triethylamine, and, at 10–20° C., 0.4 ml (4 mmol) of ethyl chloroformate in 5 ml of anhydrous methylene chloride is added dropwise. The reaction is monitored by thin-layer chromatography.

The mixture is then concentrated and the residue is taken up in methylene chloride, washed 2× with 30 ml of 0.5N NaOH, dried and concentrated. The residue is chromatographed on silica gel using methylene chloride/ethyl acetate 3:1.

Yield: 1.03 g (60% of theory); m.p.: =208° C.

The following compounds of the formula (I-1-c) were prepared similarly to Example (I-1-c-1) and in accordance with the general preparation instructions.

(I-1-c)

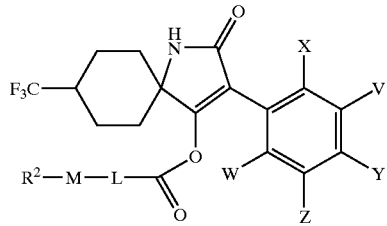

| Ex. No. | V | W | X | Y | Z | L | M | R² | m.p. ° C. | Isomer |
|---|---|---|---|---|---|---|---|---|---|---|
| I-1-c-2 | H | H | CH₃ | H | CH₃ | O | O | C₂H₅ | 177 | β |
| I-1-c-3 | H | H | CH₃ | CH₃ | CH₃ | O | O | C₂H₅ | 196 | β |
| I-1-c-4 | H | CH₃ | CH₃ | CH₃ | H | O | O | C₆H₅—CH₂— | 167 | β |
| I-1-c-5 | H | CH₃ | Cl | Cl | H | O | O | C₂H₅ | 214 | β |
| I-1-c-6 | CH₃ | CH₃ | CH₃ | CH₃ | H | O | O | C₂H₅ | 183 | β |

Example II-1

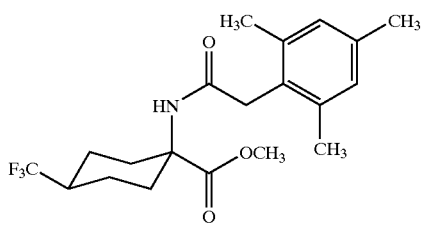

7.86 g of ethyl 1-amino4-trifluoromethyl-cyclohexane-1-carboxylate hydrochloride are initially charged in 30 ml of anhydrous acetonitrile, 13.8 g (0.1 mol) of ground potassium carbonate are added and, at 5–10° C., 5.9 g of mesitylene-acetyl chloride in 10 ml of anhydrous acetonitrile are added dropwise over a period of 10 min. The mixture is stirred at room temperature for 3 h.

The reaction solution is poured into 200 ml of ice-water and the pH is checked. After addition of seed crystals, the precipitate is filtered off with suction and taken up in methylene chloride, dried and concentrated. The residue is purified chromatographically on silica gel using methylene chloride/ethyl acetate 10:1.

Yield: 9.7 g (83.6% of theory); m.p.: =148° C.

The following compounds of the formula (II) were prepared analogously to Example II-1 and in accordance with the general preparation instructions:

(II)

$F_3C$-cyclohexane-NH-CO-CH$_2$-phenyl(V,W,X,Y,Z), CO$_2R^8$

| Ex. No. | V | W | X | Y | Z | R⁸ | m.p. ° C. | Isomer |
|---|---|---|---|---|---|---|---|---|
| II-2 | H | H | CH₃ | H | CH₃ | CH₃ | 138 | β |
| II-3 | H | H | CH₃ | CH₃ | CH₃ | CH₃ | 158 | β |
| II-4 | H | CH₃ | Cl | Cl | H | CH₃ | 145 | β |
| II-5 | CH₃ | CH₃ | CH₃ | CH₃ | H | CH₃ | 173 | β |
| II-6 | H | CH₃ | CH₃ | Cl | H | CH₃ | 181 | β |
| II-7 | H | H | Br | H | CH₃ | CH₃ | 139 | β |

Example XIV-1

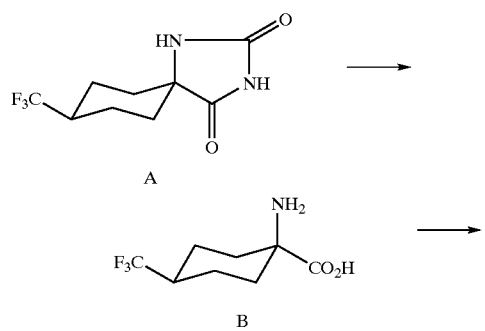

-continued

XIV-1

113.33 g (1.18 mol) of ammonium carbonate are initially charged in 337 ml of water, 25.04 g (0.51 mol) of sodium cyanide are added and 42.1 g (0.25 mol) of trifluoromethyl-cyclohexan4-one in 379 ml of ethanol are added dropwise. The reaction solution is stirred at 55–60° C. for 10 h. The pH of the mixture is then adjusted to pH 1–2 using concentrated hydrochloric acid and the precipitate is filtered off with suction and washed with water (49.3 g =83% of theory, m.p.: >250° C.). 48.7 g of the resulting hydantoin A are suspended in 270 ml of 30% strength KOH solution and stirred at reflux under protective gas for 1 day. The reaction mixture is, at 0–10° C., acidified with hydrochloric acid to pH 5.2–5.3 and the precipitate is filtered off with suction. The crude product B is then initially charged in 260 ml of anhydrous methanol, and, at 0–5° C., 21.3 ml (0.253 mol) of thionyl chloride are added dropwise. The suspension is stirred at 0° C. for 30 min and then at 40° C. for 8 h. The mixture is cooled to 0–5° C., the precipitate is filtered off with suction, washed with 15 ml of MeOH and concentrated and boiled in 40 ml of methyl tert-butyl ether, the mixture is cooled and the precipitate is filtered off with suction and dried. This gives the compound of the formula XIV-1.

Yield: 42.46 g (95% of theory), m.p.: 183° C.

Example I-2-a-1

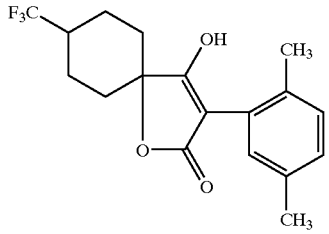

10 mmol of the compound of Example III-1 are dissolved in 5 ml of anhydrous DMF, 12 ml of 1M KOtBu solution in DMF are slowly added dropwise and the mixture is stirred at room temperature for 48 h. The mixture is concentrated using a rotary evaporator and the residue is dissolved in water, acidified with dilute hydrochloric acid and stirred for 2 h. The precipitate is filtered off with suction and dried.

Yield: 2.59 g (76% of theory), m.p.: 200–202° C.

The following compounds of the formula (I-2-a) were prepared similarly to Example (I-2-a-1) and in accordance with the general preparation instructions:

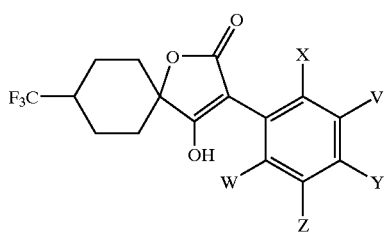

(I-2-a)

| Ex. No. | V | W | X | Y | Z | m.p. ° C. |
|---|---|---|---|---|---|---|
| I-2-a-2 | H | H | CH$_3$ | CH$_3$ | CH$_3$ | 212–214 |
| I-2-a-3 | CH$_3$ | CH$_3$ | CH$_3$ | CH$_3$ | H | 159–161 |

Example I-2-b-1

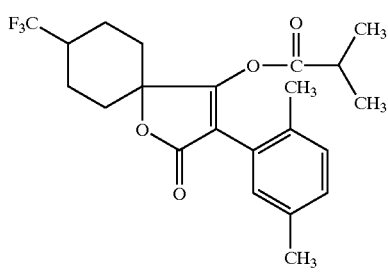

1.02 g (3 mmol) of the compound of Example I-2-a-1 are initially charged in 20 ml of anhydrous dichloromethane, 0.32 g (3.2 mmol) of triethylamine are added, and, at reflux, 0.33 g (3.1 mmol) of isobutyryl chloride in 5 ml of anhydrous dichloromethane are added dropwise. After 16 h at reflux, the mixture is concentrated and the residue is taken up in dichloromethane, washed with 0.5 N NaOH, dried and concentrated. The residue is purified chromatographically.

Yield: 1.11 g (90% of theory), oil.

$^1$H-NMR (300 MHz, CDCl$_3$): δ=1.05 (d, 6H, CH(CH$_3$)$_2$), 2.22, 2.29 (2s, 6H, Ph-CH$_3$), 2.61 (m, 1H, CH(CH$_3$)$_2$), 6.89 (s(b), 1H, Ph-6H), 7.05–7.15 (m, 2H, Ph-3H, Ph4-H) ppm.

The following compounds of the formula (I-2-b) were prepared similarly to Example (I-2-b-1) and in accordance with the general preparation instructions:

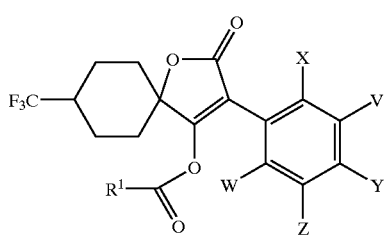

(I-2-b)

| Ex. No. | V | W | X | Y | Z | R$^1$ | m.p. ° C. |
|---|---|---|---|---|---|---|---|
| I-2-b-2 | H | H | CH$_3$ | CH$_3$ | CH$_3$ | i-C$_3$H$_7$ | oil |
| I-2-b-3 | CH$_3$ | CH$_3$ | CH$_3$ | CH$_3$ | H | i-C$_3$H$_7$ | oil |

Example III-1

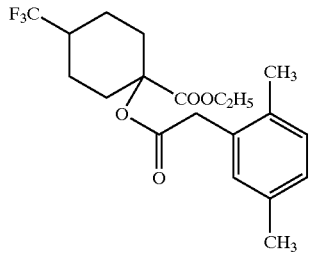

1.83 g (10 mmol) of 2,5-dimethylphenylacetyl chloride and 2.4 g (10 mmol) of ethyl 1-hydroxy-4-trifluoromethylcyclohexane-1-carboxylate are stirred at 140° C. for 8 h.

Following GC/MS analysis, the product was used without further purification for the preparation of Example I-2-a-1.

The following compounds of the formula (III) were prepared similarly to Example III-1 and in accordance with the general preparation instructions:

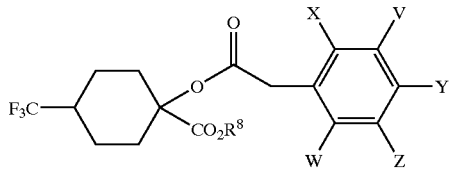

(III)

| Ex. No. | V | W | X | Y | Z | R$^8$ | m.p. ° C. |
|---|---|---|---|---|---|---|---|
| III-2* | H | H | CH$_3$ | CH$_3$ | CH$_3$ | C$_2$H$_5$ | oil |
| III-3* | CH$_3$ | CH$_3$ | CH$_3$ | CH$_3$ | H | C$_2$H$_5$ | oil |

*Following GC/MS analysis, the compounds were used without further purification for preparing compounds of the formula I-2-a.

Example XX-1

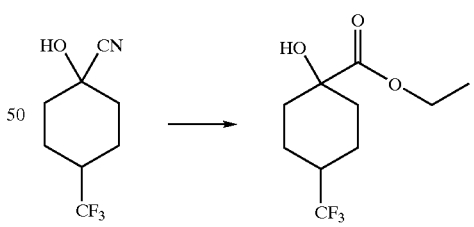

Example XX-1

55 g (0.284 mol) of the compound shown above are dissolved in 500 ml of ethanol and, at −20° C., saturated with hydrochloric acid. The mixture is stirred at 0° C. for 2 h and brought to room temperature over a period of 8 h. The mixture is degassed and concentrated and the residue is taken up in 500 ml of ice-water, stirred for 1 h and then extracted with 500 ml of dichloromethane. The organic phase is dried and concentrated.

Yield: 60 g (88% of theory), b.p. (0.05 mbar)=56° C.

USE EXAMPLES

Example A

Myzus test

Solvent: 7 parts by weight of dimethylformamide

Emulsifier: 1 part by weight of alkylaryl polyglycol ether

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) which are heavily infested by peach aphids (*Myzus persicae*) are treated by being dipped into the preparation of active compound of the desired concentration.

After the desired period of time, the kill in % is determined. 100% means that all aphids have been killed; 0% means that none of the aphids have been killed.

In this test, for example, the following compounds of the Preparation Examples show an activity which is superior to the prior art:

TABLE A

| Active compounds Example No. | Plant-damaging insects *Myzus* test | |
|---|---|---|
| | Concentration of active compound in ppm | Kill rate in % after $6^d$ |
| I-b-25 known from EP-A-596 298 | 1000 | 0 |
| I-1-b-1 according to the invention | 1000 | 95 |
| I-c-24 known from EP-A-596 298 | 1000 | 0 |
| I-1-c-1 according to the invention | 1000 | 100 |
| I-1-a-3 known from WO 97/36868 | 100 | 80 |
| I-1-a-5 according to the invention | 100 | 100 |
| I-1-a-1 known from WO 97/01535 | 1000 | 0 |
| I-1-a-3 according to the invention | 1000 | 80 |
| I-1-b-2 known from WO 97/01535 | 100 | 70 |
| I-1-b-3 according to the invention | 100 | 95 |
| I-2-a-2 known from WO 97/01535 | 1000 | 60 |
| I-2-a-2 according to the invention | 1000 | 100 |

Example B

Phaedon larvae test

Solvent: 7 parts by weight of dimethylformamide

Emulsifier: 1 part by weight of alkylaryl polyglycol ether

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with larvae of the mustard beetle (Phaedon cochleariae) while the leaves are still moist.

After the desired period of time, the kill in % is determined. 100% means that all beetle larvae have been killed; 0% means that none of the beetle larvae have been killed.

In this test, for example, the following compounds of the Preparation Examples show an activity which is superior to the prior art:

TABLE B

| Active compound Ex. No. | Plant-damaging insects *Phaedon larvae* test | |
|---|---|---|
| | Concentration of active compound in ppm | Kill rate in % after $7^d$ |
| I-b-25 known from EP-A 596 298 | 100 | 60 |
| I-1-b-1 according to the invention | 100 | 100 |
| I-1-b-4 known from WO 98/05638 | 200 | 10 |
| I-1-b-2 according to the invention | 200 | 100 |
| I-1-b-4 known from WO 97/36868 | 1000 | 0 |
| I-1-b-4 according to the invention | 1000 | 80 |
| I-1-b-2 known from WO 97/01535 | 1000 | 80 |
| I-1-b-3 according to the invention | 1000 | 100 |

Example C

*Aphis gossypii* test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and emulsifier, and the concentrate is diluted with emulsifier-containing water to the desired concentration.

Cotton leaves (*Gossypium hirsutum*) which are heavily infested by the cotton aphid (*Aphis gossypii*) are treated by being dipped into the preparation of active compound of the desired concentration.

After the desired period of time, the kill in % is determined. 100% means that all aphids have been killed; 0% means that none of the aphids have been killed.

In this test, for example, the following compound of the Preparation Examples shows an activity which is superior to the prior art:

TABLE C

| Active compound Ex. No. | Plant-damaging insects *Aphis gossypii* test | |
|---|---|---|
| | Concentration of active compound in ppm | Kill rate in % after $6^d$ |
| I-1-b-4 known from WO 98/05638 | 200 | 0 |
| I-1-b-2 according to the invention | 200 | 75 |

Example D

*Tetranychus* test (OP-resistant/dip treatment)

Solvent: 7 parts by weight of dimethylformrnamide

Emulsifier 1 part by weight of alkylaryl polyglycol ether

To produce a suitable preparation of active compound, 1 part by weight of active compound is mixed with the stated amounts of solvent and emulsifier, and the concentrate is diluted with emulsifier-containing water to the desired concentration.

Bean plants (*Phaseolus vulgaris*) which are heavily infested by all stages of the greenhouse red spider mite (*Tetranychus urticae*) are dipped into a preparation of active compound of the desired concentration.

After the desired period of time, the effect in % is determined. 100% means that all spider mites have been killed; 0% means that none of the spider mites have been killed.

In this test, for example, the following compound of the Preparation Examples shows an activity which is superior to the prior art:

TABLE D

Plant-damaging mites
*Tetranychus* test (OP-resistant/dip treatment)

| Active compound Ex. No. | Concentration of active compound in ppm | Kill rate in % after 7$^d$ |
|---|---|---|
| I-1-b-4 known from WO 97/36868 | 10 | 0 |
| I-1-b-4 according to the invention | 10 | 60 |

Example E

*Meloidogyne* test

Solvent: 7 parts by weight of dimethylformamide

Emulsifier. 1 part by weight of alkylaryl polyglycol ether

To produce a suitable preparation of active compound, 1 part by weight of active compound is mixed with the stated amounts of solvent and emulsifier, and the concentrate is diluted with water to the desired concentration.

Vessels are filled with sand, solution of active compound, *Meloidogyne incognita* egg/larvae suspension and lettuce seeds. The lettuce seeds germinate and the plants develop. On the roots, galls develop.

After the desired period of time, the nematicidal action is determined in % by the formation of galls. 100% means that no galls have been found; 0% means that the number of galls on the treated plants corresponds to that of the untreated control.

In this test, for example, the following compound of the Preparation Examples shows an activity which is superior to the prior art:

TABLE E

Plant-damaging nematodes
*Meloidogyne* test

| Active compound Ex. No. | Concentration of active compound in ppm | Kill rate in % after 7$^d$ |
|---|---|---|
| I-2-a-7 known from WO 98/05638 | 20 | 0 |
| I-2-a-1 according to the invention | 20 | 90 |

Example F

Critical concentration test/root-systemic action

Test insect: *Myzus persicae*

Solvent: 4 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

The preparation of active compound is mixed intimately with the soil. The concentration of the active compound in the preparation is virtually immaterial, only the amount by weight of active compound per volume unit of soil, which is stated in ppm (mg/ml), being decisive. The treated soil is filled into 250 ml pots and pregerminated broad beans are planted in these. Thus, the active compound can be taken up by the plant roots from the soil and then transported into the leaves.

To assess the root-systemic effect, the plants are populated with the above-mentioned test animals after 7 days. After a further 8 days, evaluation is carried out by counting or estimating the number of dead animals. The root-systemic action of the active compound is derived from the number of animals killed. It is 100% if all test animals have been killed and 0% when the number of test insects that are still alive is the same as for the untreated control.

Active compounds, application rates and results are shown in the table below:

TABLE F

Root-systemic action
*Myzus persicae*

| Active compounds (constitution) Ex. No. | Kill rate in % at active compound concentrations in ppm |
|---|---|
| Ia-11 known from EP-A-596 298 | 20 ppm = 100% |
| I-1-a-1 according to the invention | 1.25 ppm = 100% |

What is claimed is:
1. A compound of the formula (I)

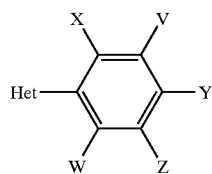

wherein

V represents hydrogen, halogen, alkyl or alkoxy, w represents hydrogen, cyano, nitro, halogen, alkyl, alkenyl, alkynyl, alkoxy, halogenoalkyl, halogenoalkoxy, optionally substituted phenyl, phenoxy, phenylthio, phenylalkoxy or phenylalkylthio, X represents halogen, alkyl, alkenyl, alkynyl, alkoxy, halogenoalkyl, halogenoalkoxy, cyano, nitro, optionally substituted phenyl, phenoxy, phenylthio, phenylalkyloxy or phenylalkylthio, Y represents hydrogen, halogen, alkyl, alkoxy, halogenoalkyl, halogenoalkoxy, cyano or nitro, Z represents hydrogen, halogen, alkyl, alkoxy, halogenoalkyl, halogenoalkoxy, hydroxyl, cyano, nitro or optionally substituted phenoxy, phenylthio, 5- or 6-membered hetaryloxy, 5- or 6-membered hetarylthio, phenylalkyloxy or phenylalkylthio, Het represents one of the groups

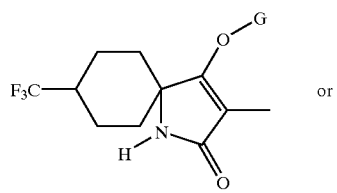

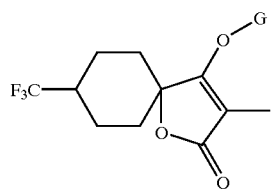

wherein

G represents hydrogen (a) or represents one of the groups

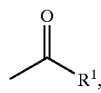

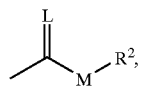

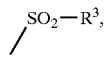

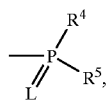

E, or

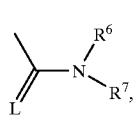

wherein

E represents hydrogen (a) or represents one of the groups

L represents oxygen or sulphur,

M represents oxygen or sulphur, $R^1$ represents optionally halogen- or cyano-substituted alkyl, alkenyl, alkoxyalkyl, alkylthioalkyl or polyalkoxyalkyl or represents optionally halogen-, alkyl- or alkoxy-substituted cycloalkyl or heterocyclyl or represents optionally substituted phenyl, phenylalkyl, hetaryl, phenoxyalkyl or hetaryloxyalkyl, $R^2$ represents optionally halogen- or cyano-substituted alkyl, alkenyl, alkoxyalkyl or polyalkoxyalkyl or represents optionally substituted cycloalkyl, phenyl or benzyl, $R^3$, $R^4$ and $R^5$ independently represent optionally halogen-substituted alkyl, alkoxy, alkylamino, dialkylamino, alkylthio, alkenylthio or cycloalkylthio or represent optionally substituted phenyl, benzyl, phenoxy or phenylthio, $R^6$ and $R^7$ independently represent hydrogen, represent optionally halogen- or cyano-substituted alkyl, cycloalkyl, alkenyl, alkoxy, alkoxyalkyl, represent optionally substituted phenyl or benzyl, or together with the N atom to which they are attached form an optionally substituted cyclic group which optionally contains oxygen or sulphur, except for the compound below

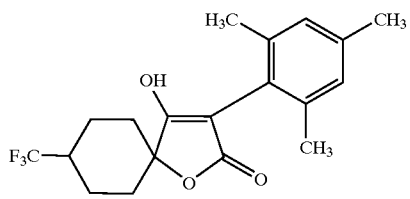

2. The compound of claim 1, wherein

V represents hydrogen, halogen, $C_1$–$C_6$-alkyl or $C_1$–$C_6$-alkoxy,

W represents hydrogen, nitro, cyano, halogen, $C_1$–$C_6$-alkyl, $C_2$–$C_6$-alkenyl or $C_2C_6$— alkynyl, $C_1$–$C_6$-alkoxy, $C_1$–$C_4$-halogenoalkyl, $C_1$–$C_4$-halogenoalkoxy or optionally halogen-, $C_1$–$C_6$-alkyl-, $C_1$–$C_6$-alkoxy-, $C_1$–$C_4$-halogenoalkyl-, $C_1$–$C_4$-halogenoalkoxy-, nitro- or cyano-substituted phenyl, phenoxy, phenylthio, phenyl-$C_1$–$C_4$-alkoxy or phenyl-$C_1$–$C_4$-alkylthio, X represents halogen, $C_1$–$C_6$-alkyl, $C_2$–$C_6$-alkenyl, $C_2$–$C_6$-alkynyl, $C_1$–$C_6$-alkoxy, $C_1$–$C_4$-halogenoalkyl, $C_1$–$C_4$-halogenoalkoxy, cyano, nitro or optionally halogen-, $C_1$–$C_6$-alkyl-, $C_1$–$C_6$-alkoxy-, $C_1$–$C_4$-halogenoalkyl-, $C_1$–$C_4$-halogenoalkoxy-, nitro- or cyano-substituted phenyl, phenoxy, phenylthio, phenyl-$C_1$–$C_4$-alkoxy or phenyl-$C_1$–$C_4$-alkylthio, Y represents hydrogen, halogen, $C_1$–$C_6$-alkyl, $C_1$–$C_6$-alkoxy, $C_1$–$C_4$-halogenoalkyl, $C_1$–$C_4$-halogenoalkoxy, cyano or nitro, Z represents hydrogen, halogen, $C_1$–$C_6$-alkyl, $C_1$–$C_6$-alkoxy, $C_1$–$C_4$-halogenoalkyl, $C_1$–$C_4$-halogenoalkoxy, hydroxyl, cyano, nitro or optionally halogen-, $C_1$–$C_4$-alkyl-, $C_1$–$C_4$-alkoxy-, $C_1$–$C_4$-halogeno-alkyl-, $C_1$–$C_4$-halogenoalkoxy-, nitro- or cyano-substituted phenoxy, phenylthio, thiazolyloxy, pyridinyloxy, pyrimidyloxy, pyrazolyloxy, phenyl-$C_1$–$C_4$-alkyloxy or phenyl-$C_1$–$C_4$-alkylthio, Het represents one of the groups

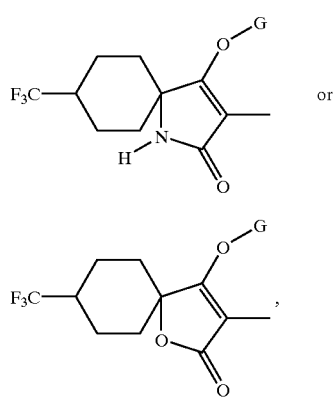

(1)

(2)

G represents hydrogen (a) or represents one of the groups

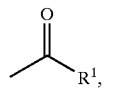

(b)

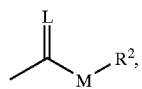

(c)

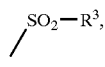

(d)

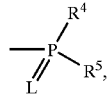

(e)

E, or (f)

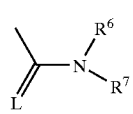

(g)

wherein

E represents a metal ion or an ammonium ion,

L represents oxygen or sulphur and

M represents oxygen or sulphur, $R^1$ represents optionally halogen- or cyano-substituted $C_1$–$C_{20}$-alkyl, $C_2$–$C_{20}$-alkenyl, $C_1$–$C_8$-alkoxy-$C_1$–$C_8$-alkyl, $C_1$–$C_8$-alkylthio-$C_1$–$C_8$-alkyl or poly-$C_1$–$C_8$-alkoxy-$C_1$–$C_8$-alkyl or represents optionally halogen-, $C_1$–$C_6$-alkyl- or $C_1$–$C_6$-alkoxy-substituted $C_3$–$C_8$-cycloalkyl in which optionally one or two not directly adjacent methylene groups are replaced by oxygen and/or sulphur, represents optionally halogen-, cyano-, nitro-, $C_1$–$C_6$-alkyl-, $C_1$–$C_6$-alkoxy-, $C_1$–$C_6$-halogenoalkyl-, $C_1$–$C_6$-halogenoalkoxy-, $C_1$–$C_6$-alkylthio- or $C_1$–$C_6$-alkylsulphonyl-substituted phenyl, represents optionally halogen-, nitro-, cyano-, $C_1$–$C_6$-alkyl-, $C_1$–$C_6$-alkoxy-, $C_1$–$C_6$-halogenoalkyl- or $C_1$–$C_6$-halogenoalkoxy-substituted phenyl-$C_1$—$C_6$-alkyl, represents optionally halogen- or $C_1$–$C_6$-alkyl-substituted 5- or 6-membered hetaryl having one or two heteroatoms selected from the group consisting of oxygen, sulphur and nitrogen, represents optionally halogen- or $C_1$–$C_6$-alkyl-substituted phenoxy-$C_1$–$C_6$-alkyl or represents optionally halogen-, amino- or $C_1$–$C_6$-alkyl-substituted 5- or 6-membered hetaryloxy-$C_1$–$C_6$-alkyl having one or two heteroatoms selected from the group consisting of oxygen, sulphur and nitrogen, $R^2$ represents optionally halogen- or cyano-substituted $C_1$–$C_{20}$-alkyl, $C_2$–$C_{20}$-alkenyl, $C_1$–$C_8$-alkoxy-$C_2$–$C_8$-alkyl or poly-$C_1$–$C_8$-alkoxy-$C_2$–$C_8$-alkyl, represents optionally halogen-, $C_1$–$C_6$-alkyl- or $C_1$–$C_6$-alkoxy-substituted $C_3$–$C_8$-cycloalkyl or represents optionally halogen-, cyano-, nitro-, $C_1$–$C_6$-alkyl-, $C_1$–$C_6$-alkoxy-, $C_1$–$C_6$-halogenoalkyl- or $C_1$–$C_6$-halogenoalkoxy-substituted phenyl or benzyl, $R^3$ represents optionally halogen-substituted $C_1$–$C_8$-alkyl or optionally halogen-, $C_1$–$C_6$-alkyl-, $C_1$–$C_6$-alkoxy-, $C_1$–$C_4$-halogenoalkyl-, $C_1$–$C_4$-halogenoalkoxy-, cyano- or nitro-substituted phenyl or benzyl, $R^4$ and $R^5$ independently represent optionally halogen-substituted $C_1$–$C_8$-alkyl, $C_1$–$C_8$-alkoxy, $C_1$–$C_8$-alkylamino, di($C_1$–$C_8$-alkyl)amino, $C_1$–$C_8$-alkylthio or $C_3$–$C_8$-alkenylthio or represent optionally halogen-, nitro-, cyano-, $C_1$–$C_4$-alkoxy-, $C_1$–$C_4$-halogenoalkoxy-, $C_1$–$C_4$-alkylthio-, $C_1$–$C_4$-halogenoalkylthio-, $C_1$—$C_4$-alkyl- or $C_1$–$C_4$-halogenoalkyl-substituted phenyl, phenoxy or phenylthio, $R^6$ and $R^7$ independently represent hydrogen, represent optionally halogen- or cyano-substituted $C_1$–$C_8$-alkyl, $C_3$–$C_8$-cycloalkyl, $C_1$—$C_8$-alkoxy, $C_3$–$C_8$-alkenyl or $C_1$–$C_8$-alkoxy-$C_2$–$C_8$-alkyl, represent optionally halogen-, $C_1$–$C_8$-alkyl-, $C_1$–$C_8$-halogenoalkyl- or $C_1$–$C_8$-alkoxy-substituted phenyl or benzyl or together represent an optionally $C_1$–$C_6$-alkyl-substituted $C_3$–$C_6$-alkylene radical in which optionally one methylene group is replaced by oxygen or sulphur, except for the compound below

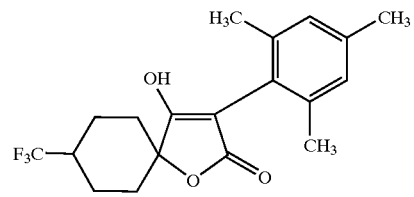

3. The compound of claim 1, wherein

V represents hydrogen, fluorine, chlorine, bromine, $C_1$–$C_4$-alkyl or $C_1$–$C_4$-alkoxy, W represents hydrogen, fluorine, chlorine, bromine, $C_1$–$C_4$-alkyl, $C_1$–$C_4$-alkoxy, $C_1$–$C_2$-halogenoalkyl or $C_1$–$C_2$-halogenoalkoxy, X represents fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, cyano or nitro, Y represents hydrogen, fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, cyano or nitro, Z represents hydrogen, fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, hydroxyl, cyano, nitro or optionally fluorine-, chlorine-, bromine-, $C_1$–$C_4$-alkyl-, $C_1$–$C_4$-alkoxy-, $C_1$–$C_2$-halogenoalkyl-, $C_1$–$C_2$-halogenoalkoxy-, nitro- or cyano-substituted phenoxy or benzyloxy, Het represents one of the groups

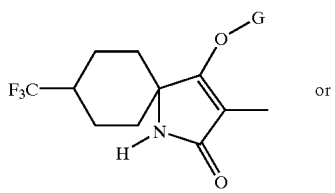
(1)

or

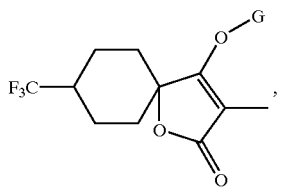
(2)

G represents hydrogen (a) or represents one of the groups

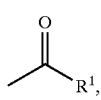
(b)

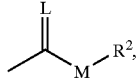
(c)

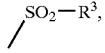
(d)

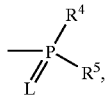
(e)

E, or
(f)

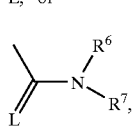
(g)

wherein

E represents a metal ion or an ammonium ion,
L represents oxygen or sulphur and
M represents oxygen or sulphur, $R^1$ represents optionally fluorine- or chlorine-substituted Cl-$C_{1-6}$-alkyl, $C_2$–$C_{16}$-alkenyl, $C_1$–$C_6$-alkoxy-$C_1$–$C_6$-alkyl, $C_1$–$C_6$-alkylthio-$C_1$–$C_6$-alkyl or poly-$C_1$–$C_6$-alkoxy-$C_1$–$C_6$-alkyl or represents optionally fluorine-, chlorine-, $C_1$–$C_5$-alkyl- or $C_1$–$C_5$-alkoxy-substituted $C_3$–$C_7$-cycloalkyl in which optionally one or two not directly adjacent methylene groups are replaced by oxygen and/or sulphur, represents optionally fluorine-, chlorine-, bromine-, cyano-, nitro-, $C_1$–$C_4$-alkyl-, $C_1$–$C_4$-alkoxy-, $C_1$–$C_3$-halogenoalkyl-, $C_1$–$C_3$-halogenoalkoxy-, $C_1$–$C_4$-alkylthio- or $C_1$–$C_4$-alkylsulphonyl-substituted phenyl, represents optionally fluorine-, chlorine-, bromine-, $C_1$–$C_4$-alkyl-, $C_1$–$C_4$-alkoxy-, $C_1$–$C_3$-halogenoalkyl- or $C_1$–$C_3$-halogenoalkoxy-substituted phenyl-$C_1$–$C_4$-alkyl, represents optionally fluorine-, chlorine-, bromine- or $C_1$–$C_4$-alkyl-substituted pyrazolyl, thiazolyl, pyridyl, pyrimidyl, furanyl or thienyl, represents optionally fluorine-, chlorine-, bromine- or $C_1$–$C_4$-alkyl-substituted phenoxy-$C_1$–$C_5$-alkyl or represents optionally fluorine-, chlorine-, bromine-, amino- or $C_1$–$C_4$-alkyl-substituted pyridyloxy-$C_1$–$C_5$-alkyl, pyrimidyloxy-$C_1$–$C_5$-alkyl or thiazolyloxy-$C_1$—$C_5$-alkyl, $R^2$ represents optionally fluorine- or chlorine-substituted Cl—$C_{1-6}$-alkyl, $C_2$–$C_{16}$-alkenyl, $C_1$–$C_6$-alkoxy-$C_2$–$C_6$-alkyl or poly-$C_1$–$C_6$-alkoxy-$C_2$–$C_6$-alkyl, represents optionally fluorine-, chlorine-, $C_1$–$C_4$-alkyl- or $C_1$–$C_4$-alkoxy-substituted $C_3$–$C_7$-cycloalkyl or represents optionally fluorine-, chlorine-, bromine-, cyano-, nitro-, $C_1$–$C_4$-alkyl-, $C_1$–$C_3$-alkoxy-, $C_1$–$C_3$-halogenoalkyl- or $C_1$–$C_3$-halogenoalkoxy-substituted phenyl or benzyl, $R^3$ represents optionally fluorine- or chlorine-substituted $C_1$–$C_6$-alkyl or optionally fluorine-, chlorine-, bromine-, $C_1$–$C_4$-alkyl-, $C_1$–$C_4$-alkoxy-, $C_1$–$C_2$-halogenoalkoxy-, $C_1$–$C_2$-halogenoalkyl-, cyano- or nitro-substituted phenyl or benzyl, $R^4$ and $R^5$ independently represent optionally fluorine- or chlorine-substituted $C_1$–$C_6$-alkyl, $C_1$–$C_6$-alkoxy, $C_1$–$C_6$-alkylamino, di($C_1$–$C_6$-alkyl)amino, $C_1$–$C_6$-alkylthio or $C_3$–$C_4$-alkenylthio or represent optionally fluorine-, chlorine-, bromine-, nitro-, cyano-, $C_1$–$C_3$-alkoxy-, $C_1$–$C_3$-halogenoalkoxy-, $C_1$–$C_3$-alkylthio-, $C_1$–$C_3$-halogenoalkylthio-, $C_1$–$C_3$-alkyl- or $C_1$–$C_3$-halogenoalkyl-substituted phenyl, phenoxy or phenylthio, $R^6$ and $R^7$ independently represent hydrogen, represent optionally fluorine- or chlorine-substituted $C_1$–$C_6$-alkyl, $C_3$–$C_6$-cycloalkyl, $C_1$–$C_6$-alkoxy, $C_3$–$C_6$-alkenyl or $C_1$–$C_6$-alkoxy-$C_2$–$C_6$-alkyl, represent optionally fluorine-, chlorine-, bromine-, $C_1$–$C_5$-halogenoalkyl-, $C_1$–$C_5$-alkyl- or $C_1$–$C_5$-alkoxy-substituted phenyl or benzyl, or together represent an optionally $C_1$–$C_4$-alkyl-substituted $C_3$–$C_6$-alkylene radical in which optionally one methylone group is replaced by oxygen or sulphur, except for the compound below

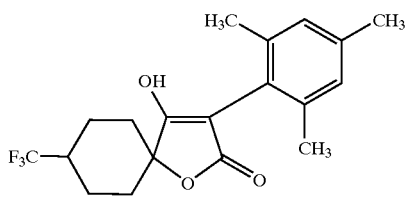

4. The compound of claim 1, wherein

V represents hydrogen, fluorine, chlorine, bromine, methyl, ethyl, methoxy or ethoxy, W represents hydrogen, fluorine, chlorine, bromine, methyl, ethyl, propyl, methoxy or ethoxy, X represents fluorine, chlorine, bromine, methyl, ethyl, propyl, isopropyl, methoxy, ethoxy, propoxy, isopropoxy, trifluoromethyl, trifluoromethoxy, difluoromethoxy or cyano, Y represents hydrogen, fluorine, chlorine, bromine, methyl, ethyl, propyl, isopropyl, tert-butyl, methoxy, ethoxy, propoxy, isopropoxy, trifluoromethyl, trifluoromethoxy, difluoromethoxy, cyano or nitro, Z represents hydrogen, fluorine, chlorine, bromine, methyl, ethyl, propyl, isopropyl, tert-butyl, methoxy, ethoxy, propoxy, isopropoxy, trifluoromethyl, trifluoromethoxy, difluoromethoxy, cyano or nitro, Het represents one of the groups

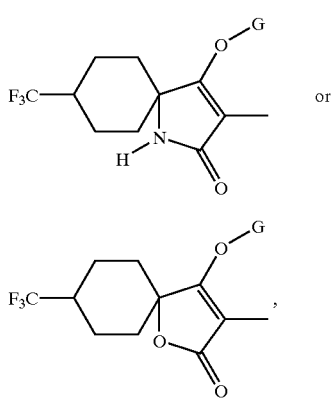

G represents hydrogen (a) or represents one of the groups

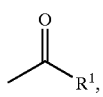

(b)

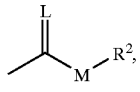

(c)

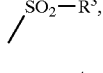

(d)

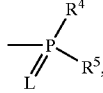

(e)

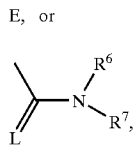

E, or (f)

(g)

wherein

E represents a metal ion or an ammonium ion,

L represents oxygen or sulphur and

M represents oxygen or sulphur, $R^1$ represents optionally fluorine- or chlorine-substituted $C_1$–$C_{14}$-alkyl, $C_2$–$C_{14}$-alkenyl, $C_1$–$C_4$-alkoxy-$C_1$–$C_6$-alkyl, $C_1$–$C_4$-alkylthio-$C_1$–$C_6$-alkyl, poly-$C_1$–$C_4$-alkoxy-$C_1$–$C_4$-alkyl or represents optionally fluorine-, chlorine-, methyl-, ethyl-, n-propyl-, isopropyl-, n-butyl-, isobutyl-, tert-butyl-, methoxy-, ethoxy-, n-propoxy- or isopropoxy-substituted $C_3$–$C_6$-cycloalkyl in which optionally one or two not directly adjacent methylene groups are replaced by oxygen and/or sulphur, represents optionally fluorine-, chlorine-, bromine-, cyano-, nitro-, methyl-, ethyl-, n-propyl-, isopropyl-, methoxy-, ethoxy-, trifluoro- methyl-, trifluoromethoxy-, methylthio-, ethylthio-, methylsulphonyl- or ethylsulphonyl-substituted phenyl, represents optionally fluorine-, chlorine-, bromine-, methyl-, ethyl-, n- propyl-, isopropyl-, methoxy-, ethoxy-, trifluoromethyl- or trifluoromethoxy-substituted benzyl, represents optionally fluorine-, chlorine-, bromine-, methyl- or ethyl-substituted furanyl, thienyl or pyridyl, represents optionally fluorine-, chlorine-, methyl- or ethyl-substituted phenoxy-$C_1$–$C_4$-alkyl or represents optionally fluorine-, chlorine-, amino-, methyl- or ethyl-substituted pyridyloxy-$C_1$–$C_4$-alkyl, pyrimidyloxy-$C_1$–$C_4$-alkyl or thiazolyloxy-$C_1$–$C_4$-alkyl, $R^2$ represents optionally fluorine or chlorine-substituted Cl —$C_{1-4}$-alkyl, $C_2$–$C_{14}$-alkenyl, $C_1$–$C_4$-alkoxy-$C_2$–$C_6$-alkyl or poly-$C_1$–$C_4$-alkoxy-$C_2$–$C_6$-alkyl, represents optionally fluorine-, chlorine-, methyl-, ethyl-, n-propyl-, isopropyl- or methoxy-substituted $C_3$–$C_6$-cycloalkyl, or represents optionally fluorine-, chlorine-, cyano-, nitro-, methyl-, ethyl-, n-propyl-, isopropyl-, methoxy-, ethoxy-, trifluoromethyl- or trifluoromethoxy-substituted phenyl or benzyl, $R^3$ represents optionally fluorine- or chlorine-substituted methyl, ethyl, propyl, isopropyl, butyl, tert-butyl, or optionally fluorine-, chlorine-, bromine-, methyl-, ethyl-, isopropyl-, tert-butyl-, methoxy-, ethoxy-, isopropoxy-, trifluoromethyl-, trifluoromethoxy-, cyano- or nitro-substituted phenyl or benzyl, $R^4$ and $R^5$ independently represent optionally fluorine- or chlorine-substituted $C_1$–$C_4$-alkyl, $C_1$–$C_4$-alkoxy, $C_1$–$C_4$-alkylamino, di($C_1$–$C_4$-alkyl)amino or $C_1$–$C_4$-alkylthio or represent optionally fluorine-, chlorine-, bromine-, nitro-, cyano-, methyl-, methoxy-, trifluoromethyl- or trifluoromethoxy-substituted phenyl, phenoxy or phenylthio, $R^6$ and $R^7$ independently represent hydrogen, represent optionally fluorine- or chlorine-substituted $C_1$–$C_4$-alkyl, $C_3$–$C_6$-cycloalkyl, $C_1$–$C_4$-alkoxy, $C_3$–$C_4$-alkenyl or $C_1$–$C_4$-alkoxy-$C_2$–$C_4$-alkyl, represent optionally fluorine-, chlorine-, bromine-, methyl-, methoxy- or trifluoromethyl-substituted phenyl or benzyl, or together represent an optionally methyl- or ethyl-substituted $C_5$–$C_6$-alkylene radical in which optionally one methylene group is replaced by oxygen or sulphur, except for the compound below

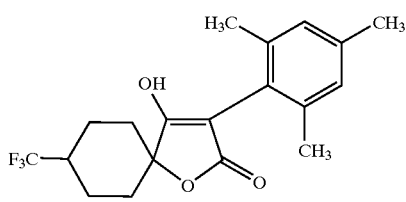

5. A process for preparing a compound of claim 1, comprising condensing intramolecularly a compound of the formula (II)

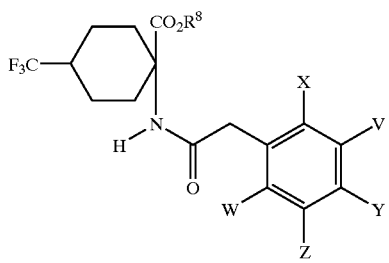

wherein
V, W, X, Y and Z are as defined in claim 1, and
$R^8$ represents alkyl
in the presence of a diluent and in the presence of a base, yielding a compound of the formula (I-1-a)

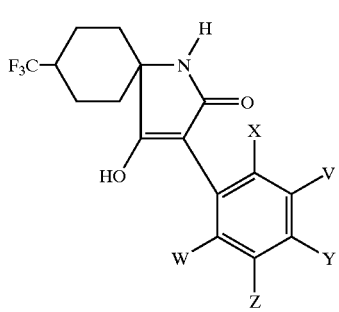

or condensing intramolecularly a compound of the formula (III)

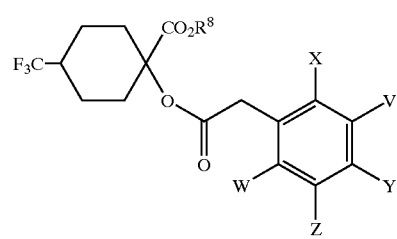

wherein
V, W, X, Y, Z and $R^8$ are as defined in claim 1,
in the presence of a diluent and in the presence of a base to yield a compound of the formula (I-2-a)

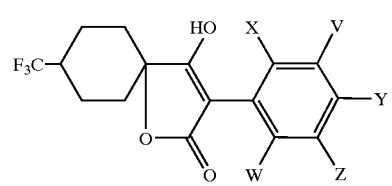

and collecting the reaction product.

6. The compound of the formula (II)

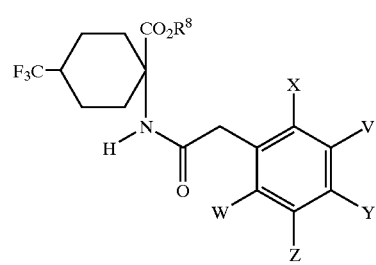

wherein
V, W, X, Y and Z are as defined in claim 1 and
$R^8$ represents alkyl.

7. The compound of the formula (III)

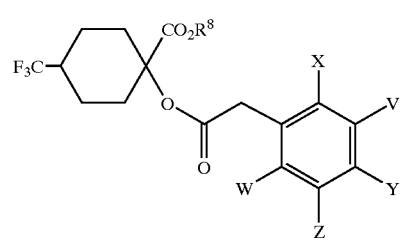

wherein

V, W, X, Y, Z and $R^8$ are as defined in claim 6 except for the compound below

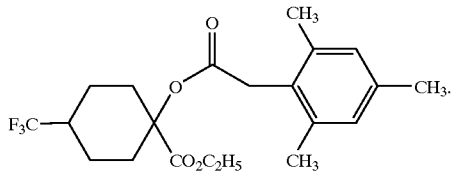

8. The compound of the formula (XVI)

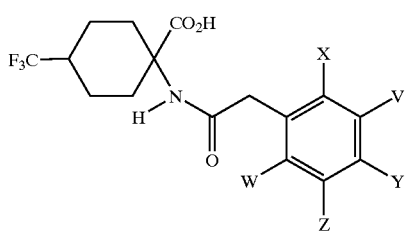

(XVI)

wherein

V, W, X, Y and Z are as defined in claim 1.

9. The compound of the formula (XIX)

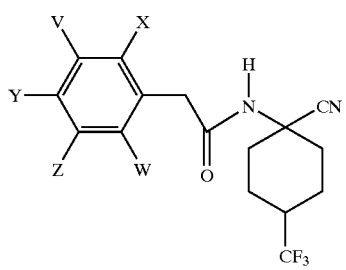

(XIX)

wherein

V, W, X, Y and Z are as defined in claim 1.

10. A compound of the formula (XVIII)

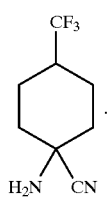

(XVIII)

11. The compound of the formula (XIV)

(XIV)

wherein $R^8$ is as defined in claim 6.

12. A pesticide and/or weed killer comprising at least one compound of claim 1.

13. A method for controlling at least one of a pest and a weed comprising applying a compound of claim 1 to the pest, weed and/or its habitat.

14. A process for preparing at least one of a pesticide and a weed killer comprising mixing at least one compound of claim 1 with at least one of extenders and surfactants.

15. The process of claim 5, further including reacting the compound of formula (I-1-a) or the compound of formula (I-2-a) with a compound of the formula (IV)

(IV)

wherein $R^1$ is as defined in claim 1 and

Hal represents halogen or reacting the compound of formula (I-1-a) or the compound of formula (I-2-a) with a compound of the formula (V)

$$R^1—CO—O—CO—R^1 \quad (V)$$

wherein $R^1$ is as defined in claim 1, and collecting the reaction product, wherein the step of reacting optionally occurs in the presence of a diluent and in the presence of an acid binder.

16. The process of claim 5, further including reacting the compound of formula (I-1-a) or the compound of formula (I-2-a) with a compound of the formula (VI)

$$R^2—M—CO—Cl \quad (VI)$$

wherein $R^2$ and M are as defined in claim 1, and collecting the reaction product, wherein the step of reacting optionally occurs in the presence of a diluent and in the presence of an acid binder.

17. The process of claim 5, further including reacting the compound of formula (I-1-a) or the compound of formula (I-2-a) with a compound of the formula (VII)

(VII)

wherein

M and $R^2$ are as defined in claim 1, and collecting the reaction product, wherein the step of reacting optionally occurs in the presence of a diluent and in the presence of an acid binder.

18. The process of claim 5, further including reacting the compound of formula (I-1-a) or the compound of formula (I-2-a) with a compound of the formula (VIII)

$$R^3—SO_2—Cl \quad (VIII)$$

wherein $R^3$ is as defined in claim 1, and collecting the reaction product, wherein the step of reacting optionally occurs in the presence of a diluent and in the presence of an acid binder.

19. The process of claim 5, further including reacting the compound of formula (I-1-a) or the compound of formula (I-2-a) with a compound of the formula (IX)

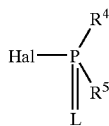 (IX)

wherein

L, $R^4$ and $R^5$ are as defined in claim 1,

Hal represents halogen, and collecting the reaction product, wherein the step of reacting optionally occurs in the presence of a diluent and in the presence of an acid binder.

20. The process of claim 5, further including reacting the compound of formula (I-1-a) or the compound of formula (I-2-a) with a compound of the formula (X) or (XI)

Me(OR$^{10}$)$_t$ (X)

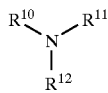 (XI)

wherein

Me represents a mono- or divalent metal, t represents the number 1 or 2 and $R^{10}$, $R^{11}$, $R^{12}$ independently represent hydrogen oralkyl, and collecting the reaction product, wherein the step of reacting optionally occurs in the presence of a diluent.

21. The process of claim 5, further including reacting the compound of formula (I-1-a) or the compound of formula (I-2-a) with a compound of the formula (XII)

 (XII)

wherein $R^6$ and L are as defined in claim 1, and collecting the reaction product, wherein the step of reacting optionally occurs in the presence of a diluent and in the presence of a catalyst, or reacting the compound of formula (I-1-a) or the compound of formula (I-2-a) with a compound of the formula (XIII)

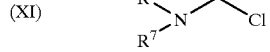 (XIII)

wherein

L, $R^6$ and $R^7$ are as defined in claim 1, and collecting the reaction product, wherein the step of reacting optionally occurs in the presence of a diluent and in the presence of an acid binder.

* * * * *